(12) United States Patent
Zhou et al.

(10) Patent No.: US 10,100,051 B2
(45) Date of Patent: Oct. 16, 2018

(54) COMPOUND OF 5-HYDROXYL-1,7-NAPHTHYRIDINE SUBSTITUTED BY ARYLOXY OR HETEROARYLOXY, PREPARATION METHOD THEREOF AND PHARMACEUTICAL USE THEREOF

(71) Applicant: SHENYANG SUNSHINE PHARMACEUTICAL CO. LTD., Shenyang, Liaoning (CN)

(72) Inventors: Yunlong Zhou, Nanjing (CN); Suixiong Cai, San Diego, CA (US); Guangfeng Wang, Shanghai (CN); Lingling Jiao, Taizhou (CN); Ping Min, Shanghai (CN); Yu Jing, Taizhou (CN); Ming Guo, San Diego, CA (US)

(73) Assignee: SHENYANG SUNSHINE PHARMACEUTICAL CO. LTD., Shenyang, Liaoning (CN)

( * ) Notice: Subject to any disclaimer, the term of this patent is extended or adjusted under 35 U.S.C. 154(b) by 0 days.

(21) Appl. No.: 15/561,471

(22) PCT Filed: Dec. 14, 2015

(86) PCT No.: PCT/CN2015/097244
§ 371 (c)(1),
(2) Date: Sep. 25, 2017

(87) PCT Pub. No.: WO2016/155357
PCT Pub. Date: Oct. 6, 2016

(65) Prior Publication Data
US 2018/0118739 A1    May 3, 2018

(30) Foreign Application Priority Data

Mar. 27, 2015 (CN) .......................... 2015 1 0140858

(51) Int. Cl.
*C07D 471/04* (2006.01)
*A61P 7/06* (2006.01)

(52) U.S. Cl.
CPC .............. *C07D 471/04* (2013.01); *A61P 7/06* (2018.01)

(58) Field of Classification Search
None
See application file for complete search history.

*Primary Examiner* — Heidi Reese
(74) *Attorney, Agent, or Firm* — Greer, Burns & Crain, Ltd.

(57) ABSTRACT

A compound of 5-hydroxyl-1,7-naphthyridine substituted by aryloxy or heteroaryloxy, a preparation method thereof and a pharmaceutical use thereof are provided. In particular, the compound has the following Formula (I), wherein $R_2$ and $R_3$ are each independently H; $R_1$ is H or $C_1$-$C_3$ alkyl; Ar is an aromatic ring or a heteroaromatic ring selected from a naphthalene ring, a pyridine ring, a thiophene ring, a furan ring and a substituted benzene ring. Pharmaceutically acceptable salts of the present compound, are provided, as well as uses of the compound or pharmaceutically acceptable salts thereof in the preparation of a medicine for inhibiting HIF prolyl hydroxylase or a medicine for promoting the generation of endogenous EPO.

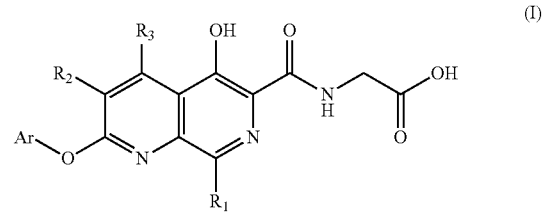

26 Claims, No Drawings

COMPOUND OF 5-HYDROXYL-1,7-NAPHTHYRIDINE SUBSTITUTED BY ARYLOXY OR HETEROARYLOXY, PREPARATION METHOD THEREOF AND PHARMACEUTICAL USE THEREOF

BACKGROUND

The present invention relates to the field of medicine, and particularly to a novel 5-hydroxyl-1,7-naphthyridine compound substituted by aryloxy or heteroaryloxy, a preparation method thereof and a pharmaceutical use thereof.

Hypoxia inducible factor (HIF) is a section of transcriptional activator containing basic helix-loop-helix (bHLH) and PAS (Per/Arnt/Sim) that responds to the hypoxia conditions by mediating a series of gene regulation in biological cells. (Chowdhury, R., Hardy, A, Schofield, C. J., The human oxygen sensing machinery and its manipulation, Chem. Soc. Rev., 2008, 37, 1308-1319; Kaelin, W. G., Jr., Ratcliffe, P. J., Oxygen sensing by metazoans: the central role of the HIF hydroxylase pathway, Mol. Cell, 2008, 30, 393-402; Schofield, C. J., Ratcliffe, P. J., Oxygen sensing by HIF hydroxylases, Nat. Rev. Mol. Cell. Biol., 2004, 5, 343-354).

In 1992, during the study of erythropoietin (EPO, an erythropoiesis-stimulating hormone), Wang et al. found the transcriptional activator that stimulates the generation of EPO in hypoxic cells, and thus named it Hypoxia Inducible Factor, abbreviated as HIF. HIF is essential for cellular adaptation and survival to hypoxia, and the experiments show that under the effect of HIF, cells can still survive even if the oxygen content in the cells is reduced to 1% from normal 20%.

HIF consists of two subunits, HIF-a and HIF-b. HIF-a contains an oxygen-dependent degradation domain (abbreviated as ODDD), which is a key element unit in response to cellular oxygen content. HIF-a can form a stable dimer with HIF-b. After this dimer enters the nucleus, it activates the expression of important enzymes or enzyme systems such as glucose metabolism-related enzymes, GLUT-1, erythropoietin and vascular endothelial growth factor (VEGF), and thus resists the cell hypoxia conditions. HIF-b is a type of aryl hydrocarbon nuclear translator (abbreviated as ARNT), which forms a heterodimer with HIF-a to activate transcription of downstream genes.

To date, three HIF-a subtypes have been discovered, HIF-1a, HIF-2a, and HIF-3a, respectively. HIF-1a, first discovered by Wang in 1995, is widely expressed in human and mouse bodies. HIF-2a was isolated and identified in 1997, which has a protein sequence with 48% similarity to that of HIF-1a and therefore has the similar functions to HIF-1a, however, HIF-2a is only expressed in lung, endothelium and carotid artery. HIF-3a is a newly discovered HIF-a subtype, and little research has been done on it yet.

Studies have shown that the expression of HIF-a in cells is not affected by oxygen content, but HIF-a cannot stably exist in the cells having normal oxygen content, and has a half-life of only 5 minutes. HIF-a can only be stable under hypoxic conditions and thus play the normal function of activation of downstream transcription factors. In the cells having normal oxygen content, the prolyl at positions 402, 564 in the ODDD region of HIF-a was oxidized by prolyl hydroxylase to form 4-hydroxyprolyl, so that HIF-a cannot be dimmed with HIF-b, but soon binds to pVHL protein and then be degraded, and therefore cannot play an anti-hypoxia function. Prolyl hydroxylase (also abbreviated as PHD or EGLN), which plays a key role in the degradation of HIF-a, is a 2-oxoglutatone (2-OG)-dependent oxygenase. With 2-OG and divalent iron ions as prosthetic groups, PHD transfers an oxygen atom to the 4-position of the prolyl molecule to form a hydroxyprolyl, and meanwhile converts 2-OG into one carbon dioxide molecule and succinic acid. Both 2-OG analogs and divalent nickel, cobalt and manganese ions can antagonize the oxidation of prolyl in HIF-a by PHD, and inhibit the degradation of HIF-a, so that HIF-a can successfully be dimmed with HIF-b, and thus stimulates the downstream transcription factors, and ultimately plays an anti-hypoxia function. Studies have found that PHD has three subtypes: PHD1, PHD2, and PHD3. Further studies suggest that inhibition on PHD1 can help to treat skeletal muscle cell degradation, can protect myofibroblasts under ischemic conditions, treat inflammatory enteritis and colitis, and treat heart failure and ischemia in patients with heart disease and kidney disease. However, no study has shown that the other two PHD subtypes have difference in functions.

One of the important roles of HIF is to activate the expression of erythropoietin (EPO) in living organisms. As a glycoprotein hormone, EPO can stimulate red blood cell proliferation, differentiation and maturation. EPO on the one hand can stimulate bone marrow hematopoietic function, timely and effectively increase the number of red blood cells, thereby enhancing the oxygen carrying capacity of the blood. On the other hand, EPO can enhance the body's oxygen binding, transport and supply capacity, and improve hypoxia conditions. Under normal physiological conditions, EPO is mainly synthesized and secreted by the kidney, therefore, a patient with kidney failure will suffer from ischemia because EPO cannot be normally synthesized in the body. In the late 1980s, Amgen company first successfully achieved industrialization of EPO and gradually applied EPO to the patients with anemia caused by chronic kidney failure, AIDS, cancer and chemotherapy. However, with the huge development of EPO generation and application, exogenous EPO administration still faces several problems: 1, EPO is expensive, and is a great burden especially for the patients who need long-term use; 2, as a macromolecule glycoprotein, EPO also has the characteristics of low bioavailability, short half-life in the organism, easy to be hydrolyzed by the enzyme in the gastrointestinal tract, so EPO must be frequently administrated by injection, which limits the probability of patient's self-administration, and brings great inconvenience to the patients; 3, Industrially synthetic EPO still cannot avoid the immunogenicity and the product has certain medication risks.

Due to these problems in the use of exogenous macromolecule EPO, it will be very promising to replace exogenous EPO and bring the patients more choices by developing small molecule HIF prolyl hydroxylase inhibitors to inhibit the HIF-a degradation, thereby stimulating the generation of endogenous EPO in human body.

So far, two HIF prolyl hydroxylases, Akebia's AKB-6548 and Fibrogen's FG-4592, have been introduced into the clinical phase II study. (Refer to WO 2012170377A1, US2010331374A1, US2010305097A1, US2007299086A1, US2004254215A1, US2007298104A1, US2009082357A1, US2010113444A1, WO2013134660, WO2010059552A1).

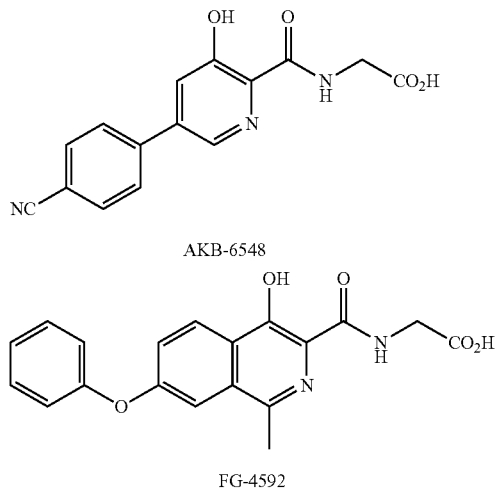

AKB-6548

FG-4592

SUMMARY

It is an object of the present invention to provide a 5-hydroxyl-1,7-naphthyridine compound substituted by aryloxy or heteroaryloxy or a salt thereof for inhibiting HIF prolyl hydroxylase.

It is another object of the present invention to provide a method for preparing the above compound.

It is another object of the present invention to provide a pharmaceutical composition comprising the above compound or a salt thereof.

It is a further object of the present invention to provide a use of the above compound or a salt thereof in preparation of a medicament.

The objects of the present invention are achieved by the following solutions:

A compound having the following Formula (I) or a pharmaceutically acceptable salt thereof:

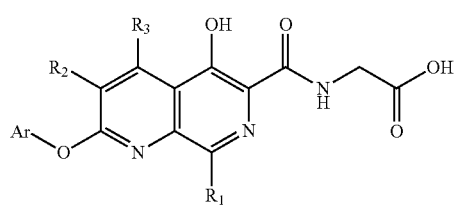

Wherein, $R_2$, $R_3$ are each independently hydrogen;

$R_1$ is hydrogen or $C_{1-3}$ alkyl;

Ar is an aromatic ring or an aromatic heterocyclic ring selected from the group consisting of a naphthalene ring, a pyridine ring, a thiophene ring, a furan ring and a substituted benzene ring.

When Ar is a substituted benzene ring, the compound of the present invention has the following Formula (II):

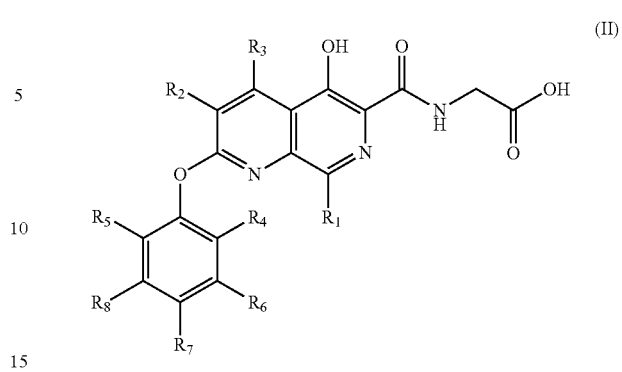

wherein $R_4$, $R_5$, $R_6$, $R_7$ and $R_8$ are independently selected from hydrogen, $C_{1-7}$ alkyl, $C_{1-3}$ alkoxy, $C_{1-3}$ alkoxy optionally substituted by halogen, $C_{1-3}$ alkyl optionally substituted by halogen, halogen, hydroxy, nitro, cyano and phenyl.

Or, when $R_6$ and $R_7$ in Formula (II) form a ring, the compound of the present invention has the following Formula (III):

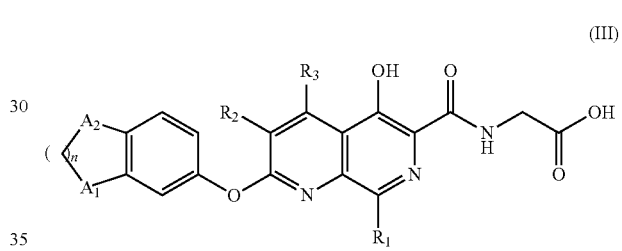

wherein, n is an integer of 1, 2, 3 or 4, and $A_1$ and $A_2$ are each independently selected from an oxygen, carbon and nitrogen atom.

The present invention also relates to a pharmaceutically acceptable salt of the compound of Formula (I), (II), (III) of the present invention, preferably, the compound reacts with a pharmaceutically acceptable base to form a pharmaceutically acceptable base addition salt. The pharmaceutically acceptable bases include, but are not limited to, sodium hydroxide, sodium carbonate, potassium hydroxide, potassium carbonate, magnesium hydroxide, magnesium oxide, calcium hydroxide, calcium oxide, diethanolamine, lysine, ethanolamine, diethylamine, piperazine and the like.

The most preferred compounds of the present invention are shown in the following table:

| No. | Structure |
|---|---|
| 1 | 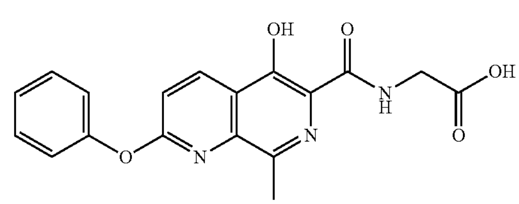 [SMILES: Cc1nc(C(=O)NCC(=O)O)c(O)c2ccc(Oc3ccccc3)nc12] |

Another aspect of the present invention provides a method for preparing a compound of Formula (I). The synthetic route of the compound is as follows:
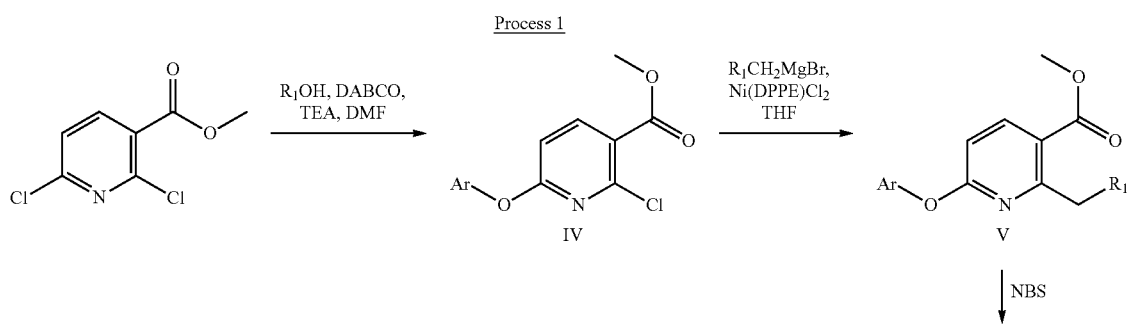

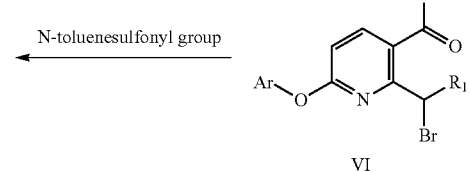

-continued

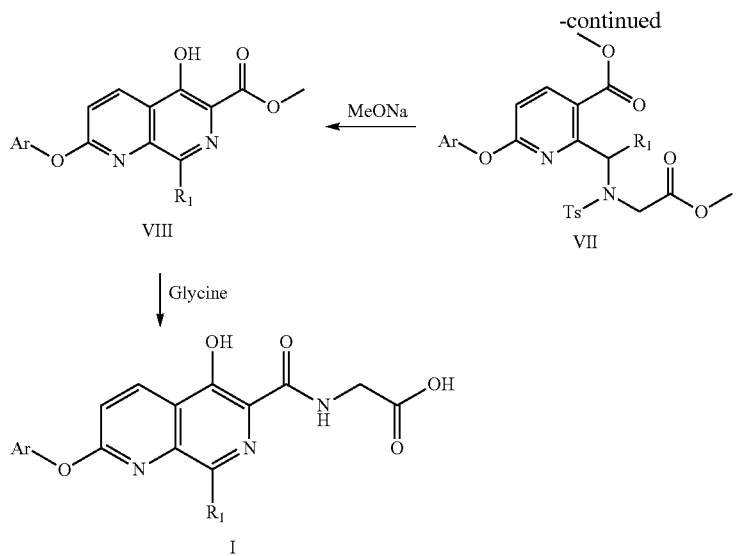

According to the present invention, a method for preparing the compound of Formula (I) of the present invention comprises:

step 1: reacting methyl 2,6-dichloropyridine-3-formate with a corresponding substituted aromatic phenol ArOH under basic conditions in the presence of a specific catalyst, to form an ether intermediate (IV);

step 2: reacting the ether intermediate (IV) obtained in the step 1 and $R_1CH_2MgBr$ in the presence of a specific catalyst to perform the replacement of the chlorine atom by the alkyl, to form a methyl 2,6-disubstituted pyridine-3-formate intermediate (V);

step 3: brominating methyl or methylene group at the 2-position in the intermediate (V) obtained in the step 2 to obtain a brominated intermediate (VI);

step 4: replacing the intermediate (VI) obtained in the step 3 with p-toluenesulfonylglycine methyl ester to obtain a p-toluenesulfonyl intermediate (VII);

step 5: subjecting the intermediate (VII) obtained in the step 4 to deprotonation at 2-methyl or methylene group of pyridine under basic conditions to form a carbon anion, followed by intramolecular attack on the carbomethoxy on pyridine ring by the carbon anion to form a ketone, and rapidly removing the p-toluenesulfonyl group under basic conditions to form a methyl 5-hydroxy-1,7-naphthyridine formate intermediate (VIII);

step 6: reacting the intermediate (VIII) obtained in the step 5 with glycine to obtain the compound of Formula (I).

In the above step 1, methyl 2,6-dichloropyridine-3-formate is reacted with a corresponding substituted aromatic phenol under basic conditions in the presence of a specific catalyst, to obtain an ether intermediate (IV). Preferred bases include triethylamine, diisopropylethylamine. Preferred catalysts include bicyclo [2.2.2]-1,4-diazacyclooctane (also known as triethylene diamine), N, N-tetramethylethylenediamine. Preferred solvents include N,N-dimethylformamide, N,N-dimethylacetamide.

In the above step 2, the intermediate (IV) prepared in step 1 is reacted with a Grignard reagent $R_1CH_2MgBr$ under a specific catalyst to perform the replacement of the chlorine atom by the alkyl, to form a methyl 2,6-disubstituted pyridine-3-formate intermediate (V). Preferred catalyst is 1,2-bis(diphenylphosphino)ethane nickel chloride (abbreviated as $Ni(DPPE)Cl_2$). Preferred reaction solvents include tetrahydrofuran, dioxane and the like. Preferred reaction temperature is 0~50° C.

In the above step 3, the methyl or methylene group at the 2-position of the pyridine of the intermediate obtained in step 2 is subjected to a free radical bromination reaction. Preferred brominating reagents include N-bromosuccinimide, dibromohydantoin, cuprous bromide, liquid bromine and the like. Preferred initiators for the bromination reaction include azobisisobutyronitrile, benzoyl peroxide and the like. Preferred solvents for the bromination reaction include carbon tetrachloride, dichloromethane and chloroform. The reaction is carried out under reflux, to obtain a bromide intermediate (VI).

In the above step 4, the intermediate (VI) obtained in step 3 is replaced by p-toluenesulfonylglycine methyl ester in the presence of a base catalyst to produce a p-toluenesulfonyl intermediate (VII). Preferred bases include potassium carbonate, cesium carbonate, sodium carbonate. Preferred reaction solvents include N,N-dimethylformamide, N-methylpyrrolidone, N, N-dimethylacetamide, dimethylsulfoxide and the like. Preferred reaction temperature is 20~80° C.

In the step 5, the p-toluenesulfonyl intermediate (VII) is subjected to intramolecular cyclization under basic conditions while the p-toluenesulfonyl group is removed to form a methyl 5-hydroxy-1,7-naphthyridine formate intermediate (VIII). Preferred bases include sodium methoxide, sodium ethoxide, potassium tert-butoxide, sodium tert-butoxide. Preferred reaction solvents include N,N-dimethylformamide, N-methylpyrrolidone, N, N-dimethylacetamide, dimethyl sulfoxide, methanol, ethanol, tetrahydrofuran and the like. Preferred reaction temperature is 0~40° C.; and preferred reaction time is 0.5~3 hours.

In the above step 6, the methyl 5-hydroxy-1,7-naphthyridine formate intermediate (VIII) is exchanged with glycine under a confined heating environment under basic conditions to directly replace methyl formate into formamido acetic acid, to form a 5-hydroxy-1,7-naphthyridine as target product (I). Preferred bases include sodium methoxide, sodium ethoxide, potassium tert-butoxide, sodium tert-butoxide and the like. Preferred reaction solvents include methanol, ethanol, isopropanol, n-butanol and the like. Preferred reaction temperature is 80~140° C.

Still another aspect of the present invention relates to a pharmaceutical composition comprising a therapeutically effective amount of a compound of Formula (I) or a pharmaceutically acceptable salt thereof, and a pharmaceutically acceptable carrier.

In another embodiment, the present invention relates to a pharmaceutical composition comprising a therapeutically effective amount of a compound of Formula (II) or a pharmaceutically acceptable salt thereof, and a pharmaceutically acceptable carrier.

In yet another embodiment, the present invention relates to a pharmaceutical composition comprising a therapeutically effective amount of a compound of Formula (III) or a pharmaceutically acceptable salt thereof, and a pharmaceutically acceptable carrier.

The present invention also relates to a use of the compound of Formula (I), (II), (III) of the invention or a pharmaceutically acceptable salt thereof in the preparation of a medicament for inhibiting HIF prolyl hydroxylase; a use of the compound of the invention in the preparation of a medicament for promoting the generation of endogenous EPO; a use of the compound of Formula (I), (II), (III) of the invention in the preparation of a medicament for stabilizing hypoxia-inducible factor α; a use of the compound of Formula (I), (II), (III) of the invention in the preparation of a medicament for treating chronic disease-related anemia in a subject, wherein the chronic disease-related anemia is selected from the group consisting of rheumatoid arthritis, rheumatic fever and inflammatory bowel disease; a use of the compound of Formula (I), (II), (III) of the invention in the preparation of a medicament for increasing the production of inflammatory cytokines in a subject, wherein the inflammatory cytokines include tumor necrosis factor, interleukin and interferon; a use of the compound of Formula (I), (II), (III) of the invention in the preparation of a medicament for treating anemia in a subject that is resistant to the treatment of exogenous erythropoietin administration, wherein the compound enhances the response of hematopoietic precursor cells to the erythropoietin; a use of the compound of Formula (I), (II), (III) of the invention in the preparation of a medicament for increasing the production of a factor required for iron ingestion, iron transport and iron utilization in a subject, wherein the factor is selected from the group consisting of erythrocyte aminolevulinic acid synthase, transferrin, transferrin receptor and plasma ceruloplasmin.

The present invention also relates to a method for inhibiting HIF prolyl hydroxylase in a subject comprising administering to the subject a compound of Formula (I), (II), (III) of the invention or a pharmaceutically acceptable salt thereof; to a method for promoting the generation of endogenous EPO in a subject comprising administering to the subject a compound of Formula (I), (II), (III) of the invention or a pharmaceutically acceptable salt thereof; to a method for stabilizing hypoxia-inducible factor α in a subject comprising administering to the subject a compound of Formula (I), (II), (II) of the invention or a pharmaceutically acceptable salt thereof; to a method for treating chronic disease-related anemia in a subject comprising administering to the subject a compound of Formula (I), (II), (III) of the invention or a pharmaceutically acceptable salt thereof, wherein the chronic disease-related anemia is selected from the group consisting of rheumatoid arthritis, rheumatic fever and inflammatory bowel disease.

The present invention also relates to a method for increasing the production of inflammatory cytokines in a subject comprising administering to the subject a compound of Formula (I), (II), (III) of the invention or a pharmaceutically acceptable salt thereof, wherein the inflammatory cytokines include tumor necrosis factor, interleukin and interferon.

A further aspect of the present invention relates to a method for treating anemia in a subject that is resistant to the treatment of exogenous erythropoietin administration comprising administering to the subject a compound of Formula (I), (II), (III) of the invention or a pharmaceutically acceptable salt thereof, wherein the compound enhances the response of hematopoietic precursor cells to the erythropoietin. The present invention also relates to a method for increasing the production of a factor required for iron ingestion, iron transport and iron utilization in a subject comprising administering to the subject a compound of Formula (I), (II), (III) of the invention or a pharmaceutically acceptable salt thereof, wherein the factor is selected from the group consisting of erythrocyte aminolevulinic acid synthase, transferrin, transferrin receptor and plasma ceruloplasmin.

DETAILED DESCRIPTION

The present invention will now be described in further detail with reference to the following examples. The following examples of the present invention are for illustrative purposes only and are not intended to limit the invention, and modifications and variations of the invention may be made without departing from the spirit of the invention and the scope of the invention as defined by the appended claims.

Example 1

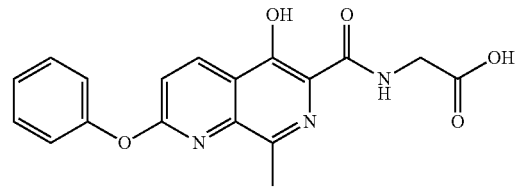 [SMILES: Cc1nc(C(=O)NCC(=O)O)c(O)c2ccc(Oc3ccccc3)nc12]

Compound No. 1 (2-(5-hydroxy-8-methyl-2-phenoxy-1,7-naphthyridine-6-formamido) acetic acid)

Step 1: Preparation of methyl 2-chloro-6-phenoxypyridine-3-formate

A 250 mL eggplant flask was sequentially charged with 8.80 g (42.72 mmol) of methyl 2,6-dichloronicotinate, 4.02 g (42.72 mmol) of phenol, and 45 mL of N,N-dimethylformamide for dissolving them. 7.80 mL (55.54 mmol) of triethylamine was added dropwise under stirring at room temperature, after completion of the dropwise addition, 720 mg (6.41 mmol) of triethylene diamine was added. The mixture was stirred at room temperature for 4-5 hours and the solution changed from clear to turbid. Thin layer chromatography [V (petroleum ether)/V (ethyl acetate)=6/1] detected that most of the raw material disappeared. Then, 1.30 mL (21.36 mmol) of HOAc, 25 mL of isopropanol and 15 mL of ice water were sequentially added while the solution changed from turbid to clear, and stirred at room temperature for 0.5 hour. 40 mL of water was slowly dropwise added, and after completion of the dropwise addition, stirred at room temperature for 2 hours. A large number of white solid precipitated and was filtered. The filter cake was washed with a mixed solution of isopropyl alcohol/water=1:1 and dried under vacuum at 50° C. for 8 hours to obtain 7.20 g of methyl 2-chloro-6-phenoxypyridine-3-formate as a solid.

Step 2: Preparation of methyl 2-ethyl-6-phenoxypyridine-3-formate

A 100 ml dry three-necked flask was sequentially charged, under the protection of argon, with 1.32 g (5 mmol) of methyl 2-chloro-6-phenoxy-pyridine-3-formate, 16 mg (0.03 mmol) of Ni (DPPE)Cl$_2$ and 5 ml of dry tetrahydrofuran for dissolving them. 11 mL (11 mmol) of ethylmagnesium bromide (1 M, in tetrahydrofuran) was slowly dropwise added under stirring at room temperature in two portions at 0.5 hour intervals, after completion of the dropwise addition, the mixture was stirred at room temperature for 0.5 hour. Thin layer chromatography [V (petroleum ether)/V (ethyl acetate)=7/1] detected that the reaction was basically completed. The reaction was quenched with 13 ml of 10% citric acid aqueous solution, and the reaction solution was partitioned between ethyl acetate and water, extracted with ethyl acetate (50 mL×2). The organic phases were combined, washed with saturated brine, dried over anhydrous sodium sulfate, and filtered. The filtrate was mixed with crude silica gel, and subjected to flash column chromatography on silica gel column, eluting with V (petroleum ether)/V (ethyl acetate)=30/1. The fraction was evaporated to dryness to obtain 1.19 g of methyl 2-ethyl-6-phenoxypyridine-3-formate as pale yellow oil.

Step 3: Preparation of methyl 2-(1-bromoethyl)-6-phenoxypyridine-3-formate

A 100 mL eggplant flask was sequentially charged with 3.20 g (12.45 mmol) of methyl 2-ethyl-6-phenoxypyridine-3-formate, 3.53 g (19.83 mmol) of N-bromosuccinimide, 3.25 g (19.83 mmol) of azobisisobutyronitrile, and 20 mL of carbon tetrachloride for dissolving them. The mixture was refluxed for 2 hours under stirring. Thin layer chromatography [V (petroleum ether)/V (ethyl acetate)=7/1] detected that the reaction was completed, and the reaction solution was partitioned between dichloromethane and water, extracted with dichloromethane (50 mL×3). The organic phases were combined, washed with saturated brine, dried over anhydrous sodium sulfate, and filtered. The filtrate was mixed with crude silica gel, and subjected to flash column chromatography on silica gel column, eluting with V (petroleum ether)/V (ethyl acetate)=30/1. The fraction was evaporated to dryness to obtain methyl 2-(1-bromoethyl)-6-phenoxypyridine-3-formate as a pale yellow oil, which was directly used in the next reaction.

Step 4: Preparation of methyl 2-(1-(N-(2-methoxy-2-oxoethyl)-4-toluenesulfonylamino)ethyl)-6-phenoxypyridine-3-formate A 100 mL eggplant flask was sequentially charged with 4.08 g (12.14 mmol) of methyl 2-(1-bromoethyl)-6-phenoxypyridine-3-formate prepared in step 3, 2.94 g (12.14 mmol) of p-toluenesulfonylglycine methyl ester, 3.35 g (24.28 mmol) of potassium carbonate and 0.18 g (1.22 mmol) of sodium iodide, and 20 mL of N,N-dimethylformamide for dissolving them. The mixture was stirred at 50° C. for 10 hours. Thin layer chromatography [V (petroleum ether)/V (ethyl acetate)=2/1] detected that the reaction was basically completed, and the reaction solution was partitioned between ethyl acetate and water, extracted with ethyl acetate (50 mL×3). The organic phases were combined, washed with saturated brine, dried over anhydrous sodium sulfate, and filtered. The filtrate was mixed with crude silica gel, and subjected to flash column chromatography on silica gel column, eluting with V (petroleum ether)/V (ethyl acetate)=4/1. The fraction was evaporated to dryness to obtain 3.26 g of methyl 2-(1-(N-(2-methoxy-2-oxoethyl)-4-toluenesulfonylamino)ethyl)-6-phenoxypyridine-3-formate as a pale yellow solid.

Step 5: Preparation of methyl 5-hydroxy-8-methyl-2-phenoxy-1,7-naphthyridine-6-formate A 50 mL single neck flask was charged with 500 mg (1 mmol) of methyl 2-(1-(N-(2-methoxy-2-oxoethyl)-4-toluenesulfonylamino)ethyl)-6-phenoxypyridine-3-formate, and 5 mL of dimethyl sulfoxide for dissolving it. A solution of 0.5 ml of sodium methoxide in methanol (5M) was dropwise added and stirred for 0.5 hour. Thin layer chromatography [V (ethyl acetate)/V (dichloromethane)=1/20)] detected that the reaction was basically completed. The reaction solution was adjusted to pH 4 with dilute hydrochloric acid, and partitioned between dichloromethane and water, extracted with dichloromethane (50 mL×2). The organic phases were combined, washed with saturated brine, dried over anhydrous sodium sulfate, and filtered. The filtrate was mixed with crude silica gel, and subjected to flash column chromatography on silica gel column, eluting with V (dichloromethane)/V (ethyl acetate)=80/1. The fraction was evaporated to dryness to obtain 200 mg of methyl 5-hydroxy-8-methyl-2-phenoxy-1,7-naphthyridine-6-formate as a white solid.

Step 6: Preparation of 2-(5-hydroxy-8-methyl-2-phenoxy-1,7-naphthyridine-6-formamido) acetic acid A 50 mL sealed reaction tube was sequentially charged with 200 mg (0.65 mmol) of methyl 5-hydroxy-8-methyl-2-phenoxy-1,7-naphthyridine-6-formate, 146 mg (1.95 mmol) of glycine, a solution of 0.5 mL of sodium methoxide in methanol (5M) and 5 mL of methanol. The mixture was stirred at 120° C. for 20 hours. LCMS detected that the reaction was basically completed. The reaction solution was adjusted with dilute hydrochloric acid to pH 4, the solution changed from yellow turbidity to clear and then back to yellow turbidity again, and a solid precipitated and was filtered. The filter cake was washed with a large amount of water and a small amount of methanol and dried to obtain 125 mg of 2-(5-hydroxy-8-methyl-2-phenoxy-1,7-naphthyridine-6-formamido) acetic acid as a yellow solid.

1H NMR (400 MHz, DMSO-d6) δ 13.28 (s, 1H), 12.85 (s, 1H), 9.12 (t, J=6.4 Hz, 1H), 8.63 (d, J=8.9 Hz, 1H), 7.57-7.46 (m, 3H), 7.41-7.28 (m, 3H), 4.05 (d, J=6.4 Hz, 2H), 2.53 (s, 3H).

Example 2

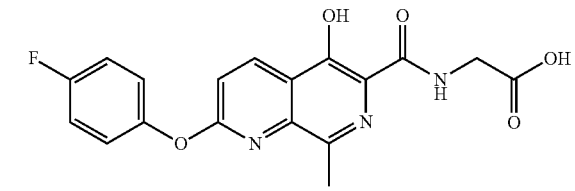 [SMILES: Cc1nc(C(=O)NCC(=O)O)c(O)c2ccc(Oc3ccc(F)cc3)nc12]

Compound No. 2 (2-(2-(4-fluorophenoxy)-5-hydroxy-8-methyl-1,7-naphthyridine-6-formamido) acetic acid

Step 1: Preparation of methyl 2-chloro-6-(4-fluorophenoxy) nicotinate

A 250 mL eggplant flask was sequentially charged with methyl 2,6-dichloronicotinate (2.06 g, 10 mmol), 4-fluorophenol (1.12 g, 10 mmol), and 12 mL of N,N-dimethylformamide for dissolving them. Triethylamine (1.80 mL, 13 mmol) was added dropwise under stirring at room temperature, after completion of the dropwise addition, triethylene diamine (168 mg, 1.50 mmol) of was added. The mixture was stirred at room temperature for 4-5 hours and the solution changed from clear to turbid. Thin layer chromatography [V (petroleum ether)/V (ethyl acetate)=6/1] detected that most of the raw material disappeared. Then, 1.30 mL of HOAc, 25 mL of isopropanol and 15 mL of ice water were sequentially added while the solution changed from turbid to clear, and stirred at room temperature for 0.5 hour. 40 mL of water was slowly dropwise added, and after completion of the dropwise addition, stirred at room temperature for 2 hours. A large number of white solid precipitated and was filtered. The filter cake was washed with a mixed solution of isopropyl alcohol/water=1:1 and dried under vacuum at 50° C. for 8 hours to obtain 2.07 g of methyl 2-chloro-6-(4-fluorophenoxy) nicotinate as a solid, 73.67%.

Step 2: Preparation of methyl 2-ethyl-6-(4-fluorophenoxy) nicotinate

A 100 ml dry three-necked flask was sequentially charged, under the protection of nitrogen, with methyl 2-chloro-6-(4-fluorophenoxy) nicotinate (1.90 g, 6.75 mmol), 1,2-bis(diphenylphosphino)ethane nickel chloride (abbreviated as Ni(DPPE)Cl$_2$) (21 mg, 0.04 mmol), and 13 ml of dry tetrahydrofuran for dissolving them. 14 mL (14 mmol) of ethylmagnesium bromide (1 M, in tetrahydrofuran) was slowly dropwise added under stirring at room temperature in two portions at 0.5 hour intervals, after completion of the dropwise addition, the mixture was stirred at room temperature for 0.5 hour. Thin layer chromatography [V (petroleum ether)/V (ethyl acetate)=7/1] detected that the reaction was basically completed. The reaction was quenched with 13 ml of 10% citric acid aqueous solution, and the reaction solution was partitioned between ethyl acetate and water, extracted with ethyl acetate (50 mL×2). The organic phases were combined, washed with saturated brine, dried over anhydrous sodium sulfate, and filtered. The filtrate was mixed with crude silica gel, and subjected to flash column chromatography on silica gel column, eluting with V (petroleum ether)/V (ethyl acetate)=30/1. The fraction was evaporated to dryness to obtain 1.45 g of methyl 2-ethyl-6-(4-fluorophenoxy) nicotinate as a pale yellow oil, 77.98%.

Step 3: Preparation of methyl 2-(1-bromoethyl)-6-(4-fluorophenoxy) nicotinate A 100 mL eggplant flask was sequentially charged with methyl 2-ethyl-6-(4-fluorophenoxy) nicotinate (1.45 g, 5.27 mmol), N-bromosuccinimide (1.03 g, 5.80 mmol), azobisisobutyronitrile (0.95 g, 5.80 mmol), and 15 ml of carbon tetrachloride for dissolving them. The mixture was refluxed for 2 hours under stirring. Thin layer chromatography [V (petroleum ether)/V (ethyl acetate)=7/1] detected that the reaction was completed, and the reaction solution was partitioned between dichloromethane and water, extracted with dichloromethane (50 mL×3). The organic phases were combined, washed with saturated brine, dried over anhydrous sodium sulfate, and filtered. The filtrate was mixed with crude silica gel, and subjected to flash column chromatography on silica gel column, eluting with V (petroleum ether)/V (ethyl acetate)=30/1. The fraction was evaporated to dryness to obtain methyl 2-(l-bromoethyl)-6-(4-fluorophenoxy) nicotinate as a pale yellow oil, which was directly used in the next reaction.

Step 4: Preparation of methyl 6-(4-fluorophenoxy)-2-(1-(N-(2-methoxy-2-oxoethyl)-4-toluenesulfonylamino) ethyl) nicotinate A 100 mL eggplant flask was sequentially charged with methyl 2-(1-bromoethyl)-6-(4-fluorophenoxy) nicotinate (1.65 g, 4.66 mmol) prepared in step 3, p-toluenesulfonylglycine methyl ester (1.13 g, 4.66 mmol) and potassium carbonate (1.29 g, 9.32 mmol) and sodium iodide (71 mg, 0.47 mmol), and 6 ml of N,N-dimethylformamide for dissolving them. The mixture was stirred at 50° C. for 10 hours. Thin layer chromatography [V (petroleum ether)/V (ethyl acetate)=2/1] detected that the reaction was basically completed, and the reaction solution was partitioned between ethyl acetate and water, extracted with ethyl acetate (50 mL×3). The organic phases were combined, washed with saturated brine, dried over anhydrous sodium sulfate, and filtered. The filtrate was mixed with crude silica gel, and subjected to flash column chromatography on silica gel column, eluting with V (petroleum ether)/V (ethyl acetate)=4/1. The fraction was evaporated to dryness to obtain 1.79 g of methyl 6-(4-fluorophenoxy)-2-(1-(N-(2-methoxy-2-oxoethyl)-4-toluenesulfonylamino)ethyl) nicotinate as a pale yellow solid, 74.43%.

Step 5: Preparation of methyl 2-(4-fluorophenoxy)-5-hydroxy-8-methyl-1,7-naphthyridine-6-carboxylate A 50 mL single neck flask was charged with methyl 6-(4-fluorophenoxy)-2-(1-(N-(2-methoxy-2-oxoethyl)-4-toluenesulfonylamino)ethyl) nicotinate (1.79 g, 3.47 mmol), and 10 mL of dimethyl sulfoxide for dissolving it. A solution of sodium methoxide in methanol (5 M, 0.8 ml, 4 mmol) was dropwise added and stirred for 0.5 hour. Thin layer chromatography [V (ethyl acetate)/V (dichloromethane)=1/20)] detected that the reaction was basically completed. The reaction solution was adjusted to pH 4 with dilute hydrochloric acid, and partitioned between dichloromethane and water, extracted with dichloromethane (50 mL×2). The organic phases were combined, washed with saturated brine, dried over anhydrous sodium sulfate, and filtered. The filtrate was mixed with crude silica gel, and subjected to flash column chromatography on silica gel column, eluting with V (dichloromethane)/V (ethyl acetate)=80/1. The fraction was evaporated to dryness to obtain 740 mg of methyl 2-(4-fluorophenoxy)-5-hydroxy-8-methyl-1,7-naphthyridine-6-carboxylate as a white solid, 65.04%.

Step 6: Preparation of 2-(2-(4-fluorophenoxy)-5-hydroxy-8-methyl-1,7-naphthyridine-6-formamido) acetic acid A 50 mL sealed reaction tube was sequentially charged with methyl 2-(4-fluorophenoxy)-5-hydroxy-8-methyl-1,7- naphthyridine-6-formate (328 mg, 1 mmol), glycine (225 mg, 3 mmol), a solution of sodium methoxide in methanol (5 M, 0.6 ml, 3 mmol) and 8 mL of methanol. The mixture was stirred at 120° C. for 20 hours. LCMS detected that the reaction was basically completed. The reaction solution was adjusted with dilute hydrochloric acid to pH 4, the solution changed from yellow turbidity to clear and then back to yellow turbidity again, and a solid precipitated and was filtered. The filter cake was washed with a large amount of water and a small amount of methanol and dried to obtain 100 mg of 2-(2-(4-fluorophenoxy)-5-hydroxy-8-methyl-1,7-naphthyridine-6-formamido) acetic acid as a yellow solid, 27%.

1H NMR (400 MHz, DMSO-d6) δ 13.27 (s, 1H), 9.13 (d, J=6.6 Hz, 1H), 8.64 (d, J=8.9 Hz, 1H), 7.55 (d, J=8.9 Hz, 1H), 7.46-7.28 (m, 4H), 4.04 (d, J=6.6 Hz, 2H), 2.53 (s, 3H).

Example 3

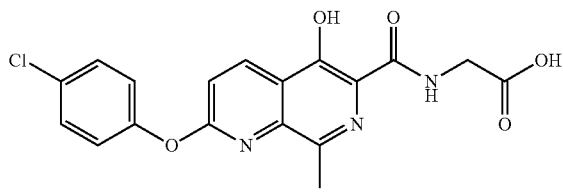 [SMILES: Cc1nc(C(=O)NCC(=O)O)c(O)c2ccc(Oc3ccc(Cl)cc3)nc12]

Compound No. 7 (2-(2-(4-chlorophenoxy)-5-hydroxy-8-methyl-1,7-naphthyridine-6-formamido) acetic acid Step 1: Preparation of methyl 2-chloro-6-(4-chlorophenoxy) nicotinate A 250 mL eggplant flask was sequentially charged with methyl 2,6-dichloronicotinate (2.06 g, 10 mmol) and 4-chlorophenol (1.57 g, 10 mmol) and 12 mL of N,N-dimethylformamide for dissolving them. Triethylamine (1.80 mL, 13 mmol) was added dropwise under stirring at room temperature, after completion of the dropwise addition, triethylene diamine (168 mg, 1.50 mmol) was added. The mixture was stirred at room temperature for 4-5 hours and the solution changed from clean to turbid. Thin layer chromatography [V (petroleum ether)/V (ethyl acetate)=6/1] detected that most of the raw material disappeared. Then, 1.30 mL of HOAc, 25 mL of isopropanol and 15 mL of ice water were sequentially added while the solution changed from turbid to clear, and stirred at room temperature for 0.5 hour. 40 mL of water was slowly dropwise added, and after completion of the dropwise addition, stirred at room temperature for 2 hours. A large number of white solid precipitated and was filtered. The filter cake was washed with a mixed solution of isopropyl alcohol/water=1:1 and dried under vacuum at 50° C. for 8 hours to obtain 2.36 g of methyl 2-chloro-6-(4-chlorophenoxy) nicotinate as a solid, 79.19%.

Step 2: Preparation of methyl 6-(4-chlorophenoxy)-2-ethyl nicotinate

A 100 ml dry three-necked flask was sequentially charged, under the protection of nitrogen, with methyl 2-chloro-6-(4-chlorophenoxy) nicotinate (2 g, 6.71 mmol), 1,2-bis(diphenylphosphino)ethane nickel chloride (abbreviated as Ni (DPPE)Cl$_2$) (21 mg, 0.04 mmol), and 13 ml of dry tetrahydrofuran for dissolving them. Ethylmagnesium bromide (1 M in tetrahydrofuran) (14 ml, 14 mmol) was slowly dropwise added under stirring at room temperature in two partitions at 0.5 hour intervals. After completion of the dropwise addition, the mixture was stirred at room temperature for 0.5 hour. Thin layer chromatography [V (petroleum ether)/V (ethyl acetate)=7/1] detected that the reaction was basically completed. The reaction was quenched with 13 ml of 10% citric acid aqueous solution, and the reaction solution was partitioned between ethyl acetate and water, extracted with ethyl acetate (50 mL×2). The organic phases were combined, washed with saturated brine, dried over anhydrous sodium sulfate, and filtered. The filtrate was mixed with crude silica gel, and subjected to flash column chromatography on silica gel column, eluting with V (petroleum ether)/V (ethyl acetate)=30/1. The fraction was evaporated to dryness to obtain 1.67 g of methyl 6-(4-chlorophenoxy)-2-ethyl nicotinate as a pale yellow oil, 85.220%.

Step 3: Preparation of methyl 2-(1-bromoethyl)-6-(4-chlorophenoxy) nicotinate

A 100 mL eggplant flask was sequentially charged with methyl 6-(4-chlorophenoxy)-2-ethyl nicotinate (1.67 g, 5.72 mmol), N-bromosuccinimide (1.12 g, 6.29 mmol), azobisisobutyronitrile (1.03 g, 6.29 mmol), and 15 mL of carbon tetrachloride for dissolving them. The mixture was refluxed for 2 hours under stirring. Thin layer chromatography [V (petroleum ether)/V (ethyl acetate)=7/1] detected that the reaction was completed, and the reaction solution was partitioned between dichloromethane and water, extracted with dichloromethane (50 mL×3). The organic phases were combined, washed with saturated brine, dried over anhydrous sodium sulfate, and filtered. The filtrate was mixed with crude silica gel, and subjected to flash column chromatography on silica gel column, eluting with V (petroleum ether)/V (ethyl acetate)=30/1. The fraction was evaporated to dryness to obtain methyl 2-(1-bromoethyl)-6-(4-chlorophenoxy) nicotinate as a pale yellow oil, which was directly used in the next reaction.

Step 4: Preparation of methyl 6-(4-chlorophenoxy)-2-(1-(N-(2-methoxy-2-oxoethyl)-4-toluenesulfonylamino)ethyl) nicotinate A 100 mL eggplant flask was sequentially charged with methyl 2-(1-bromoethyl)-6-(4-chlorophenoxy) nicotinate (1.91 g, 5.15 mmol) prepared in step 3, p-toluenesulfonyl-glycine methyl ester (1.25 g, 5.15 mmol) and potassium carbonate (1.42 g, 10.30 mmol) and sodium iodide (78 mg, 0.52 mmol), and 10 mL of N,N-dimethylformamide for dissolving them. The mixture was stirred at 50° C. for 10 hours. Thin layer chromatography [V (petroleum ether)/V (ethyl acetate)=2/1] detected that the reaction was basically completed, and the reaction solution was partitioned between ethyl acetate and water, extracted with ethyl acetate (50 mL×3). The organic phases were combined, washed with saturated brine, dried over anhydrous sodium sulfate, and filtered. The filtrate was mixed with crude silica gel, and subjected to flash column chromatography on silica gel column, eluting with V (petroleum ether)/V (ethyl acetate)=4/1. The fraction was evaporated to dryness to obtain 1.20 g of methyl 6-(4-chlorophenoxy)-2-(1-(N-(2-methoxy-2-oxoethyl)-4-toluenesulfonylamino) ethyl) nicotinate as a pale yellow solid, 43.73%.

Step 5: Preparation of methyl 2-(4-chlorophenoxy)-5-hydroxy-8-methyl-1,7-naphthyridine-6-carboxylate A 50 mL single neck flask was charged with methyl 6-(4-chlorophenoxy)-2-(1-(N-(2-methoxy-2-oxoethyl)-4-toluenesulfonylamino) ethyl) nicotinate (1.20 g, 2.25 mmol) was added and dissolved in 10 mL of dimethyl sulfoxide. A solution of sodium methoxide in methanol (5 M, 0.9 ml, 4.5 mmol) was dropwise added and stirred for 0.5 hour. Thin layer chromatography [V (ethyl acetate)/V (dichloromethane)=1/20)] detected that the reaction was basically completed. The reaction solution was adjusted to pH 4 with dilute hydrochloric acid, and partitioned between dichloromethane and water, extracted with dichloromethane (50 mL×2). The organic phases were combined, washed with saturated brine, dried over anhydrous sodium sulfate, and filtered. The filtrate was mixed with crude silica gel, and subjected to flash column chromatography on silica gel column, eluting with V (dichloromethane)/V (ethyl acetate) =80/1. The fraction was evaporated to dryness to obtain 530 mg of methyl 2-(4-chlorophenoxy)-5-hydroxy-8-methyl-1,7-naphthyridine-6-carboxylate as a white solid, 71.77%.

Step 6: Preparation of 2-(2-(4-chlorophenoxy)-5-hydroxy-8-methyl-1,7-naphthyridine-6-formamido) acetic acid A 50 mL sealed reaction tube was sequentially charged with methyl 2-(4-chlorophenoxy)-5-hydroxy-8-methyl-1,7-naphthyridine-6-carboxylate (350 mg, 1.02 mmol), glycine (225 mg, 3.06 mmol), a solution of sodium methoxide in methanol (5 M, 0.6 ml, 3 mmol) and 6 mL of methanol. The mixture was stirred at 120° C. for 20 hours. LCMS detected that the reaction was basically completed. The reaction solution was adjusted with dilute hydrochloric acid to pH 4, the solution changed from yellow turbidity to clear and then back to yellow turbidity, and a solid precipitated and was filtered. The filter cake was washed with a large amount of water and a small amount of methanol and dried to obtain 50 mg of 2-(2-(4-chlorophenoxy)-5-hydroxy-8-methyl-1,7-naphthyridine-6-formamido) acetic acid as a yellow solid, 12.11%.

1H NMR (400 MHz, DMSO-d6) δ 13.29 (s, 1H), 9.12 (t, J=6.2 Hz, 1H), 8.66 (d, J=8.9 Hz, 1H), 7.60-7.58 (m, 3H), 7.47-7.39 (m, 2H), 4.04 (d, J=6.2 Hz, 2H), 2.54 (s, 3H).

Example 4

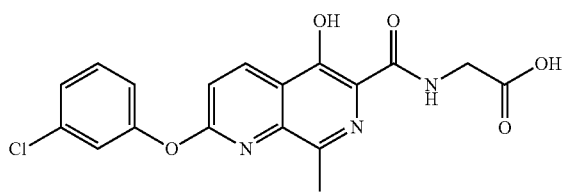 [SMILES: Cc1nc(C(=O)NCC(=O)O)c(O)c2ccc(Oc3cccc(Cl)c3)nc12]

Compound No. 3 2-(2-(3-chlorophenoxy)-5-hydroxy-8-methyl-1,7-naphthyridine-6-formamido) acetic acid Step 1: Preparation of methyl 2-chloro-6-(3-chlorophenoxy) nicotinate A 250 mL eggplant flask was sequentially charged with methyl 2,6-dichloronicotinate (2.06 g, 10 mmol), 3-chlorophenol (1.28 g, 10 mmol) and 12 mL of N,N-dimethylformamide for dissolving them. Triethylamine (1.80 ml, 13 mmol) was added dropwise under stirring at room temperature, and after completion of the dropwise addition, triethylene diamine (168 mg, 1.50 mmol) was added. The mixture was stirred at room temperature for 4-5 hours and the solution changed from clear to turbid. Thin layer chromatography [V (petroleum ether)/V (ethyl acetate)=6/1] detected that most of the raw material disappeared. Then, 1.30 mL of HOAc, 25 mL of isopropanol and 15 mL of ice water were sequentially added while the solution changed from turbid to clear, and stirred at room temperature for 0.5 hour. 40 mL of water was slowly dropwise added, and after completion of the dropwise addition, stirred at room temperature for 2 hours. A large number of white solid precipitated and was filtered. The filter cake was washed with a mixed solution of isopropyl alcohol/water=1:1 and dried under vacuum at 50° C. for 8 hours to obtain 1.77 g of methyl 2-chloro-6-(3-chlorophenoxy) nicotinate as a solid, 59.40%.

Step 2: Preparation of methyl 6-(3-chlorophenoxy)-2-ethylnicotinate

A 100 ml dry three-necked flask was sequentially charged, under the protection of nitrogen, with methyl 2-chloro-6-(3-chlorophenoxy) nicotinate (1.77 g, 5.94 mmol), 1,2-bis(diphenylphosphino)ethane nickel chloride (abbreviated as Ni(DPPE)Cl$_2$) (16 mg, 0.03 mmol) and 10 ml of dry tetrahydrofuran for dissolving them. Ethylmagnesium bromide (1 M, in tetrahydrofuran) (12 mL, 12 mmol) was slowly dropwise added under stirring at room temperature in two portions at 0.5 hour intervals, and after completion of the dropwise addition, the mixture was stirred at room temperature for 0.5 hour. Thin layer chromatography [V (petroleum ether)/V (ethyl acetate)=7/1] detected that the reaction was basically completed. The reaction was quenched with 13 ml of 10% citric acid aqueous solution, and the reaction solution was partitioned between ethyl acetate and water, extracted with ethyl acetate (50 mL×2). The organic phases were combined, washed with saturated brine, dried over anhydrous sodium sulfate, and filtered. The filtrate was mixed with crude silica gel, and subjected to flash column chromatography on silica gel column, eluting with V (petroleum ether)/V (ethyl acetate)=30/1. The fraction was evaporated to dryness to obtain 1.51 g of methyl 6-(3-chlorophenoxy)-2-ethylnicotinate as a pale yellow oil, 87.06%.

Step 3: Preparation of methyl 2-(1-bromoethyl)-6-(3-chlorophenoxy) nicotinate

A 100 mL eggplant flask was sequentially charged with methyl 6-(3-chlorophenoxy)-2-ethylnicotinate (1.51 g, 5.17 mmol), N-bromosuccinimide (1.01 g, 5.69 mmol), azobisisobutyronitrile (0.94 g, 5.69 mmol), and 15 mL of carbon tetrachloride for dissolving them. The mixture was refluxed for 2 hours under stirring. Thin layer chromatography [V (petroleum ether)/V (ethyl acetate)=7/1] detected that the reaction was completed, and the reaction solution was partitioned between dichloromethane and water, extracted with dichloromethane (50 mL<3). The organic phases were combined, washed with saturated brine, dried over anhydrous sodium sulfate, and filtered. The filtrate was mixed with crude silica gel, and subjected to flash column chromatography on silica gel column, eluting with V (petroleum ether)/V (ethyl acetate)=30/1. The fraction was evaporated to dryness to obtain methyl 2-(1-bromoethyl)-6-(3-chlorophenoxy) nicotinate as a pale yellow oil, which was directly used in the next reaction.

Step 4: Preparation of methyl 6-(3-chlorophenoxy)-2-(1-(N-(2-methoxy-2-oxoethyl)-4-toluenesulfonylamino)ethyl) nicotinate A 100 mL eggplant flask was sequentially charged with methyl 2-(1-bromoethyl)-6-(4-chlorophenoxy) nicotinate (1.54 g, 4.15 mmol) prepared in step 3, p-toluenesulfonyl-glycine methyl ester (1.00 g, 4.15 mmol) and potassium carbonate (1.15 g, 8.30 mmol) and sodium iodide (63 mg, 0.42 mmol) and 10 ml of N,N-dimethylformamide for dissolving them. The mixture was stirred at 50° C. for 10 hours. Thin layer chromatography [V (petroleum ether)/V (ethyl acetate)=2/1] detected that the reaction was basically completed, and the reaction solution was partitioned between ethyl acetate and water, extracted with ethyl acetate (50 mL×3). The organic phases were combined, washed with saturated brine, dried over anhydrous sodium sulfate, and filtered. The filtrate was mixed with crude silica gel, and subjected to flash column chromatography on silica gel column, eluting with V (petroleum ether)/V (ethyl acetate)=4/1. The fraction was evaporated to dryness to obtain 0.52 g of methyl 6-(3-chlorophenoxy)-2-(1-(N-(2-methoxy-2-oxoethyl)-4-toluenesulfonylamino)ethyl) nicotinate as a pale yellow solid, 23.50%.

Step 5: Preparation of methyl 2-(3-chlorophenoxy)-5-hydroxy-8-methyl-1, 7-naphthyridine-6-carboxylate A 50 mL single neck flask was charged with methyl 6-(3-chlorophenoxy)-2-(1-(N-(2-methoxy-2-oxoethyl)-4-toluenesulfonylamino) ethyl) nicotinate (520 mg, 0.98 mmol) and 10 mL of dimethyl sulfoxide for dissolving it. A solution of sodium methoxide in methanol (5 M, 0.4 ml, 2 mmol) was dropwise added and stirred for 0.5 hour. Thin layer chromatography [V (ethyl acetate)/V (dichloromethane)=1/20] detected that the reaction was basically completed. The reaction solution was adjusted to pH 4 with dilute hydrochloric acid, and partitioned between dichloromethane and water, extracted with dichloromethane (50 mL×2). The organic phases were combined, washed with saturated brine, dried over anhydrous sodium sulfate, and filtered. The filtrate was mixed with crude silica gel, and subjected to flash column chromatography on silica gel column, eluting with V (dichloromethane)/V (ethyl acetate)=80/1. The fraction was evaporated to dryness to obtain 250 mg of methyl 2-(3-chlorophenoxy)-5-hydroxy-8-methyl-1,7-naphthyridine-6-carboxylate as a white solid, 78.12%.

Step 6: Preparation of 2-(2-(3-chlorophenoxy)-5-hydroxy-8-methyl-1,7-naphthyridine-6-formamido) acetic acid A 50 mL sealed reaction tube was sequentially charged with methyl 2-(3-chlorophenoxy)-5-hydroxy-8-methyl-1,7-naphthyridine-6-carboxylate (180 mg, 0.55 mmol), glycine (124 mg, 1.65 mmol), a solution of sodium methoxide in methanol (5 M, 0.4 ml, 2 mmol) and 6 mL of methanol. The mixture was stirred at 120° C. for 20 hours. LCMS detected that the reaction was basically completed. The reaction solution was adjusted with dilute hydrochloric acid to pH 4, the solution changed from yellow turbidity to clear and then back to yellow turbidity again, and a solid precipitated and was filtered. The filter cake was washed with a large amount of water and a small amount of methanol and dried to obtain 30 mg of 2-(2-(3-chlorophenoxy)-5-hydroxy-8-methyl-1,7-naphthyridine-6-formamido) acetic acid as a yellow solid, 14.13%.

1H NMR (400 MHz, DMSO-d6) δ 13.30 (s, 1H), 12.83 (s, 1H), 9.14 (t, J=6.2 Hz, 1H), 8.66 (d, J=9.0 Hz, 1H), 7.61-7.50 (m, 3H), 7.41-7.35 (m, 2H), 4.05 (d, J=6.2 Hz, 2H), 2.55 (s, 3H).

Example 5

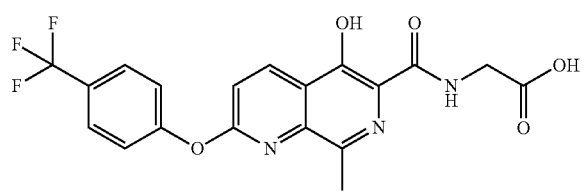 [SMILES: Cc1nc(C(=O)NCC(=O)O)c(O)c2ccc(Oc3ccc(C(F)(F)F)cc3)nc12]

Compound No. 8 (2-5-hydroxy-8-methyl-2-(4-(trifluoromethyl)phenoxy)-1,7-naphthyridine-6-formamido) acetic acid Step 1: Preparation of methyl 2-chloro-6-(4-(trifluoromethyl)phenoxy) nicotinate A 250 mL eggplant flask was sequentially charged with methyl 2,6-dichloronicotinate (2.06 g, 10 mmol), 4-(trifluoromethyl) phenol (1.62 g, 10 mmol), and 12 mL of N,N-dimethylformamide for dissolving them. Triethylamine (1.8 mL, 13 mmol) was added dropwise under stirring at room temperature, and after completion of the dropwise addition, triethylene diamine (168 mg, 1.50 mmol) was added. The mixture was stirred at room temperature for 4-5 hours and the solution changed from clear to turbid. Thin layer chromatography [V (petroleum ether)/V (ethyl acetate)=6/1] detected that most of the raw material disappeared. Then, 1.30 mL of HOAc, 25 mL of isopropanol and 15 mL of ice water were sequentially added while the solution changed from turbid to clear, and stirred at room temperature for 0.5 hour. 40 mL of water was slowly dropwise added, and after completion of the dropwise addition, stirred at room temperature for 2 hours. A large number of white solid precipitated and was filtered. The filter cake was washed with a mixed solution of isopropyl alcohol/water=1:1 and dried under vacuum at 50° C. for 8 hours to obtain 1.75 g of methyl 2-chloro-6-(4-(trifluoromethyl) phenoxy) nicotinate, 52.87%.

Step 2: Preparation of methyl 2-ethyl-6-(4-(trifluoromethyl)phenoxy) nicotinate

A 100 ml dry three-necked flask was sequentially charged, under the protection of nitrogen, with methyl 2-chloro-6-(4-(trifluoromethyl)phenoxy) nicotinate (1.75 g, 5.29 mmol), 1,2-bis(diphenylphosphino)ethane nickel chloride (abbreviated as Ni(DPPE)Cl₂) (16 mg, 0.03 mmol) and 10 ml of dry tetrahydrofuran for dissolving them. 11 mL (11 mmol) of ethylmagnesium bromide (1 M, in tetrahydrofuran) was slowly dropwise added under stirring at room temperature in two portions at 0.5 hour intervals, and after completion of the dropwise addition, the mixture was stirred at room temperature for 0.5 hour. Thin layer chromatography [V (petroleum ether)/V (ethyl acetate)=7/1] detected that the reaction was basically completed. The reaction was quenched with 13 ml of 10% citric acid aqueous solution, and the reaction solution was partitioned between ethyl acetate and water, extracted with ethyl acetate (50 mL×2). The organic phases were combined, washed with saturated brine, dried over anhydrous sodium sulfate, and filtered. The filtrate was mixed with crude silica gel, and subjected to flash column chromatography on silica gel column, eluting with V (petroleum ether)/V (ethyl acetate)=30/1. The fraction was evaporated to dryness to obtain 1.43 g of methyl 2-ethyl-6-(4-(trifluoromethyl)phenoxy) nicotinate as a pale yellow oil, 83.22%.

Step 3: Preparation of methyl 2-(1-bromoethyl)-6-(4-(trifluoromethyl) phenoxy) nicotinate A 100 mL eggplant flask was sequentially charged with methyl 2-ethyl-6-(4-(trifluoromethyl)phenoxy) nicotinate (1.43 g, 4.40 mmol), N-bromosuccinimide (862 mg, 4.84 mmol), azobisisobutyronitrile (794 mg, 4.84 mmol) and 15 ml of carbon tetrachloride for dissolving them. The mixture was refluxed for 2 hours under stirring. Thin layer chromatography [V (petroleum ether)/V (ethyl acetate)=7/1] detected that the reaction was completed, and the reaction solution was partitioned between dichloromethane and water, extracted with dichloromethane (50 mL×3). The organic phases were combined, washed with saturated brine, dried over anhydrous sodium sulfate, and filtered. The filtrate was mixed with crude silica gel, and subjected to flash column chromatography on silica gel column, eluting with V (petroleum ether)/V (ethyl acetate)=30/1. The fraction was evaporated to dryness to obtain methyl 2-(1-bromoethyl)-6-(4-(trifluoromethyl)phenoxy) nicotinate as a pale yellow oil, which was directly used in the next reaction.

Step 4: Preparation of methyl 2-(1-(N-(2-methoxy-2-oxoethyl)-4-toluenesulfonylamino) ethyl)-6-(4-(trifluoromethyl) phenoxy) nicotinate A 100 mL eggplant flask was sequentially charged with methyl 2-(1-bromoethyl)-6-(4-(trifluoromethyl)phenoxy) nicotinate (1.42 g, 3.51 mmol) prepared in step 3, p-toluenesulfonylglycine methyl ester (850 mg, 3.51 mmol) and potassium carbonate (970 mg, 7.02 mmol) and sodium iodide (53 mg, 0.35 mmol) and 10 ml of N,N-dimethylformamide for dissolving them. The mixture was stirred at 50° C. for 10 hours. Thin layer chromatography [V (petroleum ether)/V (ethyl acetate)=2/1] detected that the reaction was basically completed, and the reaction solution was partitioned between ethyl acetate and water, extracted with ethyl acetate (50 mL×3). The organic phases were combined, washed with saturated brine, dried over anhydrous sodium sulfate, and filtered. The filtrate was mixed with crude silica gel, and subjected to flash column chromatography on silica gel column, eluting with V (petroleum ether)/V (ethyl acetate)=4/1. The fraction was evaporated to dryness to obtain 1.08 g of methyl 2-(1-(N-(2-methoxy-2-oxoethyl)-4-toluenesulfonylamino)ethyl)-6-(4-(trifluoromethyl)phenoxy) nicotinate, 54.29%.

Step 5: Preparation of methyl 5-hydroxy-8-methyl-2-(4-(trifluoromethyl) phenoxy)-1,7-naphthyridine-6-carboxylate A 50 mL single neck flask was charged with methyl 2-(1-(N-(2-methoxy-2-oxoethyl)-4-toluenesulfonylamino) ethyl)-6-(4-(trifluoromethyl)phenoxy) nicotinate (310 mg, 0.55 mmol) and 5 mL of dimethyl sulfoxide for dissolving it. A solution of sodium methoxide in methanol (5 M, 0.3 ml, 1.5 mmol) was dropwise added and stirred for 0.5 hour. Thin layer chromatography [V (ethyl acetate)/V (dichloromethane)=1/20)] detected that the reaction was basically completed. The reaction solution was adjusted to pH 4 with dilute hydrochloric acid, and partitioned between dichloromethane and water, extracted with dichloromethane (50 mL×2). The organic phases were combined, washed with saturated brine, dried over anhydrous sodium sulfate, and filtered. The filtrate was mixed with crude silica gel, and subjected to flash column chromatography on silica gel column, eluting with V (dichloromethane)/V (ethyl acetate)=80/1. The fraction was evaporated to dryness to obtain 130 mg of methyl 5-hydroxy-8-methyl-2-(4-(trifluoromethyl)phenoxy)-1,7-naphthyridine-6-carboxylate as a white solid, 62.79%.

Step 6: Preparation of 2-(5-hydroxy-8-methyl-2-(4-(trifluoromethyl) phenoxy)-1,7-naphthyridine-6-formamido) acetic acid A 50 mL sealed reaction tube was sequentially charged with methyl 5-hydroxy-8-methyl-2-(4-(trifluoromethyl)phenoxy)-1,7-naphthyridine-6-carboxylate (130 mg, 0.36 mmol), glycine (81 mg, 1.08 mmol), a solution of sodium methoxide (5 M, 0.2 mL, 1 mmol) in methanol and 5 mL of methanol. The mixture was stirred at 120° C. for 20 hours. LCMS detected that the reaction was basically completed. The reaction solution was adjusted with dilute hydrochloric acid to pH 4, the solution changed from yellow turbidity to clear and then back to yellow turbidity, and a solid precipitated and was filtered. The filter cake was washed with a large amount of water and a small amount of methanol and dried to obtain 32 mg of 2-(5-hydroxy-8-methyl-2-(4-(trifluoromethyl)phenoxy)-1,7-naphthyridine-6-formamido) acetic acid as a yellow solid, 22.10%.

1H NMR (400 MHz, DMSO-d6) δ 13.31 (s, 1H), 12.84 (s, 1H), 9.15 (t, J=6.2 Hz, 1H), 8.69 (d, J=8.9 Hz, 1H), 7.94-7.85 (m, 2H), 7.68-7.59 (m, 3H), 4.05 (d, J=6.2 Hz, 2H), 2.54 (s, 3H).

Example 6

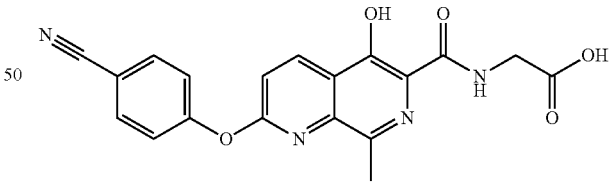

Compound No. 4 (2-(2-(4-cyanophenoxy)-5-hydroxy-8-methyl-1,7-naphthyridine-6-formamido) acetic acid)

Step 1: Preparation of methyl 2-chloro-6-(4-cyanophenoxy) nicotinate

A 250 mL eggplant flask was sequentially charged with methyl 2,6-dichloronicotinate (2.06 g, 10 mmol), 4-hydroxybenzonitrile (1.20 g, 10 mmol), and 12 mL of N,N-dimethylformamide for dissolving them. Triethylamine (1.80 ml, 13 mmol) was added dropwise under stirring at room temperature, and after completion of the dropwise addition, triethylene diamine (168 mg, 1.50 mmol) was added. The mixture was stirred at room temperature for 4-5 hours and the solution changed from clear to turbid. Thin layer chromatography [V (petroleum ether)/V (ethyl acetate) =6/1] detected that most of the raw material disappeared. Then, 1.30 mL of HOAc, 25 mL of isopropanol and 15 mL of ice water were sequentially added while the solution changed from turbid to clear, and stirred at room temperature for 0.5 hour. 40 mL of water was slowly dropwise added, and after completion of the dropwise addition, stirred at room temperature for 2 hours. A large number of white solid precipitated and was filtered. The filter cake was washed with a mixed solution of isopropyl alcohol/water=1:1 and dried under vacuum at 50° C. for 8 hours to obtain 1.94 g of methyl 2-chloro-6-(4-cyanophenoxy) nicotinate as a solid, 67.36%.

Step 2: Preparation of methyl 6-(4-cyanophenoxy)-2-ethylnicotinate

A 100 ml dry three-necked flask was sequentially charged, under the protection of nitrogen, with methyl 2-chloro-6-(4-cyanophenoxy) nicotinate (1.94 g, 6.74 mmol), 1,2-bis (diphenylphosphino)ethane nickel chloride (abbreviated as Ni(DPPE)Cl$_2$) (16 mg, 0.03 mmol) and 15 ml of dry tetrahydrofuran for dissolving them. 7 mL (7 mmol) of ethylmagnesium bromide (1 M, in tetrahydrofuran) was slowly dropwise added under stirring at room temperature in two portions at 0.5 hour intervals, and after completion of the dropwise addition, the mixture was stirred at room temperature for 0.5 hour. Thin layer chromatography [V (petroleum ether)/V (ethyl acetate)=7/1] detected that the reaction was basically completed. The reaction was quenched with 13 ml of 10% citric acid aqueous solution, and the reaction solution was partitioned between ethyl acetate and water, extracted with ethyl acetate (50 mL×2). The organic phases were combined, washed with saturated brine, dried over anhydrous sodium sulfate, and filtered. The filtrate was mixed with crude silica gel, and subjected to flash column chromatography on silica gel column, eluting with V (petroleum ether)/V (ethyl acetate)=30/1. The fraction was evaporated to dryness to obtain 1.23 g of methyl 6-(4-cyanophenoxy)-2-ethylnicotinate as a pale yellow oil, 64.75%.

Step 3: Preparation of methyl 2-(1-bromoethyl)-6-(4-cyanophenoxy) nicotinate

A 100 mL eggplant flask was sequentially charged with methyl 6-(4-cyanophenoxy)-2-ethylnicotinate (1.23 g, 4.36 mmol), N-bromosuccinimide (0.85 g, 4.80 mmol), azobisisobutyronitrile (0.79 g, 4.80 mmol) and 15 ml of carbon tetrachloride for dissolving them. The mixture was refluxed for 2 hours under stirring. Thin layer chromatography [V (petroleum ether)/V (ethyl acetate)=7/1] detected that the reaction was completed, and the reaction solution was partitioned between dichloromethane and water, extracted with dichloromethane (50 mL×3). The organic phases were combined, washed with saturated brine, dried over anhydrous sodium sulfate, and filtered. The filtrate was mixed with crude silica gel, and subjected to flash column chromatography on silica gel column, eluting with V (petroleum ether)/V (ethyl acetate)=30/1. The fraction was evaporated to dryness to obtain methyl 2-(1-bromoethyl)-6-(4-cyanophenoxy) nicotinate as a pale yellow oil, which was directly used in the next reaction.

Step 4: Preparation of methyl 6-(4-cyanophenoxy)-2-(1-(N-(2-methoxy-2-oxoethyl)-4-toluenesulfonylamino)ethyl) nicotinate A 100 mL eggplant flask was sequentially charged with methyl 2-(1-bromoethyl)-6-(4-cyanophenoxy) nicotinate (1.30 g, 3.60 mmol) prepared in step 3, p-toluenesulfonylglycine methyl ester (871 mg, 3.60 mmol) and potassium carbonate (994 mg, 7.20 mmol) and sodium iodide (54 mg, 0.36 mmol) and 15 ml of N,N-dimethylformamide for dissolving them. The mixture was stirred at 50° C. for 10 hours. Thin layer chromatography [V (petroleum ether)/V (ethyl acetate)=2/1] detected that the reaction was basically completed, and the reaction solution was partitioned between ethyl acetate and water, extracted with ethyl acetate (50 mL×3). The organic phases were combined, washed with saturated brine, dried over anhydrous sodium sulfate, and filtered. The filtrate was mixed with crude silica gel, and subjected to flash column chromatography on silica gel column, eluting with V (petroleum ether)/V (ethyl acetate)=4/1. The fraction was evaporated to dryness to obtain 0.89 g of methyl 6-(4-cyanophenoxy)-2-(1-(N-(2-methoxy-2-oxoethyl)-4-toluenesul fonylamino)ethyl) nicotinate, 47.26%.

Step 5: Preparation of methyl 2-(4-cyanophenoxy)-5-hydroxy-8-methyl-1,7-naphthyridine-6-carboxylate A 50 mL single neck flask was charged with methyl 6-(4-cyanophenoxy)-2-(1-(N-(2-methoxy-2-oxoethyl)-4-toluenesulfonylamino)ethyl) nicotinate (890 mg, 1.70 mmol) and 8 mL of dimethyl sulfoxide for dissolving it. A solution of sodium methoxide in methanol (5 M, 0.7 ml, 3.5 mmol) was dropwise added and stirred for 0.5 hour. Thin layer chromatography [V (ethyl acetate)/V (dichloromethane)=1/20)] detected that the reaction was basically completed. The reaction solution was adjusted to pH 4 with dilute hydrochloric acid, and partitioned between dichloromethane and water, extracted with dichloromethane (50 mL×2). The organic phases were combined, washed with saturated brine, dried over anhydrous sodium sulfate, and filtered. The filtrate was mixed with crude silica gel, and subjected to flash column chromatography on silica gel column, eluting with V (dichloromethane)/V (ethyl acetate)=80/1. The fraction was evaporated to dryness to obtain 370 mg of methyl 2-(4-cyanophenoxy)-5-hydroxy-8-methyl-1,7-naphthyridine-6-carboxylate as a white solid, 57.52%.

Step 6: Preparation of 2-(2-(4-cyanophenoxy)-5-hydroxy-8-methyl-1,7-naphthyridine-6-formamido) acetic acid A 50 mL sealed reaction tube was sequentially charged with methyl 2-(4-cyanophenoxy)-5-hydroxy-8-methyl-1,7-naphthyridine-6-carboxylate (110 mg, 0.33 mmol), glycine (75 mg, 1 mmol), a solution of sodium methoxide in methanol (5 M, 0.2 ml, 1 mmol) and 5 mL of methanol. The mixture was stirred at 120° C. for 20 hours. LCMS detected that the reaction was basically completed. The reaction solution was adjusted with dilute hydrochloric acid to pH 4, the solution changed from yellow turbidity to clear and then back to yellow turbidity, and a solid precipitated and was filtered. The filter cake was washed with a large amount of water and a small amount of methanol and dried to obtain 30 mg of 2-(2-(4-cyanophenoxy)-5-hydroxy-8-methyl-1,7-naphthyridine-6-formamido) acetic acid as a yellow solid, 24.17%.

1H NMR (400 MHz, DMSO-d6) δ 13.31 (s, 1H), 9.14 (t, J=6.2 Hz, 1H), 8.69 (d, J=9.0 Hz, 1H), 8.05-7.97 (m, 2H), 7.67-7.59 (m, 3H), 4.04 (d, J=6.2 Hz, 2H), 2.54 (s, 3H).

Example 7

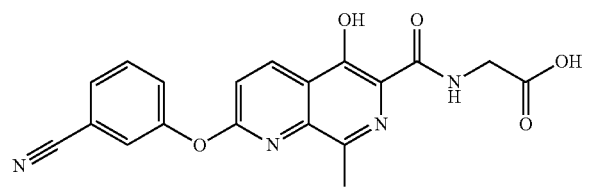 [SMILES: Cc1nc(C(=O)NCC(=O)O)c(O)c2ccc(Oc3cccc(C#N)c3)nc12]

Compound No. 9 2-(2-(3-cyanophenoxy)-5-hydroxy-8-methyl-1,7-naphthyridine-6-formamido) acetic acid Step 1: Preparation of methyl 2-chloro-6-(3-cyanophenoxy) nicotinate A 250 mL eggplant flask was sequentially charged with methyl 2,6-dichloronicotinate (3.09 g, 15 mmol), 3-hydroxybenzonitrile (1.79 g, 15 mmol), and 18 mL of N,N-dimethylformamide for dissolving them. Triethylamine (2.7 mL, 6.5 mmol) was added dropwise under stirring at room temperature, and after completion of the dropwise addition, triethylene diamine (252 mg, 0.75 mmol) was added. The mixture was stirred at room temperature for 4-5 hours and the solution changed from clear to turbid. Thin layer chromatography [V (petroleum ether)/V (ethyl acetate)=6/1] detected that most of the raw material disappeared. Then, 1.30 mL of HOAc, 25 mL of isopropanol and 15 mL of ice water were sequentially added while the solution changed from turbid to clear, and stirred at room temperature for 0.5 hour. 40 mL of water was slowly dropwise added, and after completion of the dropwise addition, stirred at room temperature for 2 hours. A large number of white solid precipitated and was filtered. The filter cake was washed with a mixed solution of isopropyl alcohol/water=1:1 and dried under vacuum at 50° C. for 8 hours to obtain 3.51 g of methyl 2-chloro-6-(3-cyanophenoxy) nicotinate as a solid, 81.25%.

Step 2: Preparation of methyl 6-(3-cyanophenoxy)-2-ethylnicotinate

A 100 ml dry three-necked flask was sequentially charged, under the protection of nitrogen, with methyl 2-chloro-6-(3-cyanophenoxy) nicotinate (3.51 g, 12.16 mmol), 1,2-bis(diphenylphosphino)ethane nickel chloride (abbreviated as Ni(DPPE)Cl$_2$) (33 mg, 0.06 mmol) and 20 ml of dry tetrahydrofuran for dissolving them. 25 mL (25 mmol) of ethylmagnesium bromide (1 M, in tetrahydrofuran) was slowly dropwise added under stirring at room temperature in two portions at 0.5 hour intervals, and after completion of the dropwise addition, the mixture was stirred at room temperature for 0.5 hour. Thin layer chromatography [V (petroleum ether)/V (ethyl acetate)=7/1] detected that the reaction was basically completed. The reaction was quenched with 13 ml of 10% citric acid aqueous solution, and the reaction solution was partitioned between ethyl acetate and water, extracted with ethyl acetate (50 mL×2). The organic phases were combined, washed with saturated brine, dried over anhydrous sodium sulfate, and filtered. The filtrate was mixed with crude silica gel, and subjected to flash column chromatography on silica gel column, eluting with V (petroleum ether)/V (ethyl acetate)=30/1. The fraction was evaporated to dryness to obtain 3.40 g of methyl 6-(3-cyanophenoxy)-2-ethylnicotinate as a pale yellow oil, 98.93%.

Step 3: Preparation of methyl 2-(1-bromoethyl)-6-(3-cyanophenoxy) nicotinate

A 100 mL eggplant flask was sequentially charged with methyl 6-(3-cyanophenoxy)-2-ethylnicotinate (3.40 g, 12.06 mmol), N-bromosuccinimide (2.36 g, 13.27 mmol), azobisisobutyronitrile (2.18 g, 13.27 mmol) and 20 ml of carbon tetrachloride for dissolving them. The mixture was refluxed for 2 hours under stirring. Thin layer chromatography [V (petroleum ether)/V (ethyl acetate)=7/1] detected that the reaction was completed, and the reaction solution was partitioned between dichloromethane and water, extracted with dichloromethane (50 mL<3). The organic phases were combined, washed with saturated brine, dried over anhydrous sodium sulfate, and filtered. The filtrate was mixed with crude silica gel, and subjected to flash column chromatography on silica gel column, eluting with V (petroleum ether)/V (ethyl acetate)=30/1. The fraction was evaporated to dryness to obtain methyl 2-(1-bromoethyl)-6-(3-cyanophenoxy) nicotinate as a pale yellow oil, which was directly used in the next reaction.

Step 4: Preparation of methyl 6-(3-cyanophenoxy)-2-(1-(N-(2-methoxy-2-oxoethyl)-4-toluenesulfonylamino) ethyl) nicotinate A 100 mL eggplant flask was sequentially charged with methyl 2-(1-bromoethyl)-6-(3-cyanophenoxy) nicotinate (4.34 g, 12 mmol) prepared in step 3, p-toluenesulfonylglycine methyl ester (2.90 g, 12 mmol) and potassium carbonate (3.31 g, 24 mmol) and sodium iodide (180 mg, 1.2 mmol) and 20 ml of N,N-dimethylformamide for dissolving them. The mixture was stirred at 50° C. for 10 hours. Thin layer chromatography [V (petroleum ether)/V (ethyl acetate)=2/1] detected that the reaction was basically completed, and the reaction solution was partitioned between ethyl acetate and water, extracted with ethyl acetate (50 mL×3). The organic phases were combined, washed with saturated brine, dried over anhydrous sodium sulfate, and filtered. The filtrate was mixed with crude silica gel, and subjected to flash column chromatography on silica gel column, eluting with V (petroleum ether)/V (ethyl acetate)=4/1. The fraction was evaporated to dryness to obtain 3.05 g of methyl 6-(3-cyanophenoxy)-2-(1-(N-(2-methoxy-2-oxoethyl)-4-toluenesulfonylamino)ethyl) nicotinate, 48.51%.

Step 5: Preparation of methyl 2-(3-cyanophenoxy)-5-hydroxy-8-methyl-1,7-naphthyridine-6-carboxylate A 50 mL single neck flask was charged with methyl 6-(3-cyanophenoxy)-2-(1-(N-(2-methoxy-2-oxoethyl)-4-toluenesulfonylamino) ethyl) nicotinate (3.05 g, 5.83 mmol) and 15 mL of dimethyl sulfoxide for dissolving it. A solution of sodium methoxide in methanol (5 M, 2.4 ml, 12 mmol) was dropwise added and stirred for 0.5 hour. Thin layer chromatography [V (ethyl acetate)/V (dichloromethane)=1/20)] detected that the reaction was basically completed. The reaction solution was adjusted to pH 4 with dilute hydrochloric acid, and partitioned between dichloromethane and water, extracted with dichloromethane (50 mL×2). The organic phases were combined, washed with saturated brine, dried over anhydrous sodium sulfate, and filtered. The filtrate was mixed with crude silica gel, and subjected to flash column chromatography on silica gel column, eluting with V (dichloromethane)/V (ethyl acetate)=80/1. The fraction was evaporated to dryness to obtain 1.80 g of methyl 2-(3-cyanophenoxy)-5-hydroxy-8-methyl-1,7-naphthyridine-6-carboxylate as a white solid, 92.14%.

Step 6: Preparation of 2-(2-(4-cyanophenoxy)-5-hydroxy-8-methyl-1,7-naphthyridine-6-formamido) acetic acid A 50 mL sealed reaction tube was sequentially charged with methyl 2-(3-cyanophenoxy)-5-hydroxy-8-methyl-1,7-naphthyridine-6-carboxylate (250 mg, 0.75 mmol), glycine (124 mg, 2.25 mmol), a solution of sodium methoxide in methanol (5 M, 0.5 ml, 2.25 mmol) and 5 mL of methanol. The mixture was stirred at 120° C. for 20 hours. LCMS detected that the reaction was basically completed. The reaction solution was adjusted with dilute hydrochloric acid to pH 4, the solution changed from yellow turbidity to clear and then back to yellow turbidity, and a solid precipitated and was filtered. The filter cake was washed with a large amount of water and a small amount of methanol and dried to obtain 90 mg of 2-(2-(3-cyanophenoxy)-5-hydroxy-8-methyl-1,7-naphthyridine-6-formamido) acetic acid as a yellow solid, 31.90%.

1H NMR (400 MHz, DMSO-d6) δ 13.31 (s, 1H), 12.85 (s, 1H), 9.14 (t, J=6.2 Hz, 1H), 8.68 (d, J=8.9 Hz, 1H), 8.02-7.97 (m, 1H), 7.86-7.66 (m, 3H), 7.62 (d, J=8.9 Hz, 1H), 4.04 (d, J=6.2 Hz, 2H), 2.52 (s, 3H).

Example 8

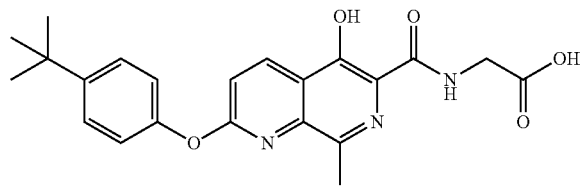 [SMILES: Cc1nc(C(=O)NCC(=O)O)c(O)c2ccc(Oc3ccc(C(C)(C)C)cc3)nc12]

Compound No. 5 2-(2-(4-(tert-butyl)phenoxy)-5-hydroxy-8-methyl-1,7-naphthyridine-6-formamido) acetic acid Step 1: Preparation of methyl 6-(4-(tert-butyl)phenoxy)-2-chloronicotinate A 250 mL eggplant flask was sequentially charged with methyl 2,6-dichloronicotinate (2.06 g, 10 mmol), 4-(tert-butyl) phenol (1.50 g, 10 mmol), and 12 mL of N,N-dimethylformamide for dissolving them. Triethylamine (1.80 mL, 13 mmol) was added dropwise under stirring at room temperature, and after completion of the dropwise addition, triethylene diamine (168 mg, 1.50 mmol) was added. The mixture was stirred at room temperature for 4-5 hours and the solution changed from clear to turbid. Thin layer chromatography [V (petroleum ether)/V (ethyl acetate)=6/1] detected that most of the raw material disappeared. Then, 1.30 mL of HOAc, 25 mL of isopropanol and 15 mL of ice water were sequentially added while the solution changed from turbid to clear, and stirred at room temperature for 0.5 hour. 40 mL of water was slowly dropwise added, and after completion of the dropwise addition, stirred at room temperature for 2 hours. A large number of white solid precipitated and was filtered. The filter cake was washed with a mixed solution of isopropyl alcohol/water=1:1 and dried under vacuum at 50° C. for 8 hours to obtain 2.60 g of methyl 6-(4-(tert-butyl)phenoxy)-2-chloronicotinate as a solid, 81.50%.

Step 2: Preparation of methyl 6-(4-(tert-butyl)phenoxy)-2-ethylnicotinate

A 100 ml dry three-necked flask was sequentially charged, under the protection of nitrogen, with methyl 6-(4-(tert-butyl) phenoxy)-2-chloronicotinate (2.60 g, 8.13 mmol), 1,2-bis(diphenylphosphino)ethane nickel chloride (abbreviated as Ni(DPPE)Cl$_2$) (22 mg, 0.04 mmol) and 15 ml of dry tetrahydrofuran for dissolving them. 17 mL (17 mmol) of ethylmagnesium bromide (1 M, in tetrahydrofuran) was slowly dropwise added under stirring at room temperature in two portions at 0.5 hour intervals, and after completion of the dropwise addition, the mixture was stirred at room temperature for 0.5 hour. Thin layer chromatography [V (petroleum ether)/V (ethyl acetate)=7/1] detected that the reaction was basically completed. The reaction was quenched with 13 ml of 10% citric acid aqueous solution, and the reaction solution was partitioned between ethyl acetate and water, extracted with ethyl acetate (50 mL×2). The organic phases were combined, washed with saturated brine, dried over anhydrous sodium sulfate, and filtered. The filtrate was mixed with crude silica gel, and subjected to flash column chromatography on silica gel column, eluting with V (petroleum ether)/V (ethyl acetate)=30/1. The fraction was evaporated to dryness to obtain 2.19 g of methyl 6-(4-(tert-butyl)phenoxy)-2-ethylnicotinate as a pale yellow oil, 85.85%.

Step 3: Preparation of methyl 2-(1-bromoethyl)-6-(4-(tert-butyl)phenoxy) nicotinate A 100 mL eggplant flask was sequentially charged with methyl 6-(4-(tert-butyl)phenoxy)-2-ethylnicotinate (2.19 g, 6.99 mmol), N-bromosuccinimide (1.37 g, 7.69 mmol), azobisisobutyronitrile (1.26 g, 7.69 mmol) and 15 ml of carbon tetrachloride for dissolving them. The mixture was refluxed for 2 hours under stirring. Thin layer chromatography [V (petroleum ether)/V (ethyl acetate)=7/1] detected that the reaction was completed, and the reaction solution was partitioned between dichloromethane and water, extracted with dichloromethane (50 mL×3). The organic phases were combined, washed with saturated brine, dried over anhydrous sodium sulfate, and filtered. The filtrate was mixed with crude silica gel, and subjected to flash column chromatography on silica gel column, eluting with V (petroleum ether)/V (ethyl acetate)=30/1. The fraction was evaporated to dryness to methyl 2-(1-bromoethyl)-6-(4-(tert-butyl)phenoxy) nicotinate as a pale yellow oil, which was directly used in the next reaction.

Step 4: Preparation of methyl 6-(4-(tert-butyl)phenoxy)-2-(1-(N-(2-methoxy-2-oxoethyl)-4-toluenesulfonylamino)ethyl) nicotinate A 100 mL eggplant flask was sequentially charged with methyl 2-(1-bromoethyl)-6-(4-(tert-butyl)phenoxy) nicotinate (2.48 g, 6.32 mmol) prepared in step 3, p-toluenesulfonylglycine methyl ester (1.53 g, 6.32 mmol) and potassium carbonate (1.75 g, 12.64 mmol) and sodium iodide (95 mg, 0.63 mmol) and 15 ml of N,N-dimethylformamide for dissolving them. The mixture was stirred at 50° C. for 10 hours. Thin layer chromatography [V (petroleum ether)/V (ethyl acetate)=2/1] detected that the reaction was basically completed, and the reaction solution was partitioned between ethyl acetate and water, extracted with ethyl acetate (50 mL×3). The organic phases were combined, washed with saturated brine, dried over anhydrous sodium sulfate, and filtered. The filtrate was mixed with crude silica gel, and subjected to flash column chromatography on silica gel column, eluting with V (petroleum ether)/V (ethyl acetate)=4/1. The fraction was evaporated to dryness to obtain 0.93 g of methyl 6-(4-(tert-butyl)phenoxy)-2-(1-(N-(2-methoxy-2-oxoethyl)-4-toluenesulfonylamino) ethyl) nicotinate, 26.49%.

Step 5: Preparation of methyl 2-(4-(tert-butyl)phenoxy)-5-hydroxy-8-methyl-1,7-naphthyridine-6-carboxylate A 50 mL single neck flask was charged with methyl 6-(4-(tert-butyl) phenoxy)-2-(1-(N-(2-methoxy-2-oxoethyl)-4-toluenesulfonylamino)ethyl) nicotinate (930 mg, 1.68 mmol) and 8 mL of dimethyl sulfoxide for dissolving it. A solution of sodium methoxide in methanol (5 M, 0.7 ml, 3.5 mmol) was dropwise added and stirred for 0.5 hour. Thin layer chromatography [V (ethyl acetate)/V (dichloromethane)=1/20)] detected that the reaction was basically completed. The reaction solution was adjusted to pH 4 with dilute hydrochloric acid, and partitioned between dichloromethane and water, extracted with dichloromethane (50 mL×2). The organic phases were combined, washed with saturated brine, dried over anhydrous sodium sulfate, and filtered. The filtrate was mixed with crude silica gel, and subjected to flash column chromatography on silica gel column, eluting with V (dichloromethane)/V (ethyl acetate)=80/1. The fraction was evaporated to dryness to obtain 420 mg of methyl 2-(4-(tert-butyl)phenoxy)-5-hydroxy-8-methyl-1,7-naphthyridine-6-carboxylate as a white solid, 68.48%.

Step 6: Preparation of 2-(2-(4-(tert-butyl)phenoxy)-5-hydroxy-8-methyl-1,7-naphthyridine-6-formamido) acetic acid A 50 mL sealed reaction tube was sequentially charged with methyl 2-(4-(tert-butyl)phenoxy)-5-hydroxy-8-methyl-1,7-naphthyridine-6-carboxylate (360 mg, 1 mmol), glycine (169 mg, 3 mmol), a solution of sodium methoxide in methanol (5 M, 0.6 ml, 3 mmol) and 6 mL of methanol. The mixture was stirred at 120° C. for 20 hours. LCMS detected that the reaction was basically completed. The reaction solution was adjusted with dilute hydrochloric acid to pH 4, the solution changed from yellow turbidity to clear and then back to yellow turbidity, and a solid precipitated and was filtered. The filter cake was washed with a large amount of water and a small amount of methanol and dried to obtain 140 mg of 2-(2-(4-(tert-butyl)phenoxy)-5-hydroxy-8-methyl-1,7-naphthyridine-6-formamido) acetic acid as a yellow solid, 34.80%.

1H NMR (400 MHz, DMSO-d6) δ 13.29 (s, 1H), 9.11 (t, J=6.2 Hz, 1H), 8.63 (d, J=9.0 Hz, 1H), 7.55-7.45 (m, 3H), 7.34-7.25 (m, 2H), 4.03 (d, J=6.2 Hz, 2H), 2.58 (s, 3H), 1.34 (s, 9H).

Example 9

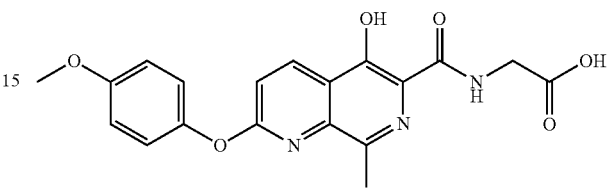

Compound No. 14: 2-(5-hydroxy-2-(4-methoxyphenoxy)-8-methyl-1,7-naphthyridine-6-formamido) acetic acid

Step 1: Preparation of methyl 2-chloro-6-(4-methoxyphenoxy) nicotinate

A 250 mL eggplant flask was sequentially charged with methyl 2,6-dichloronicotinate (3.09 g, 15 mmol), 4-methoxyphenol (1.86 g, 15 mmol), and 18 mL of N,N-dimethylformamide for dissolving them. Triethylamine (2.7 ml, 19.5 mmol) was added dropwise under stirring at room temperature, and after completion of the dropwise addition, triethylene diamine (252 mg, 2.25 mmol) was added. The mixture was stirred at room temperature for 4-5 hours and the solution changed from clear to turbid. Thin layer chromatography [V (petroleum ether)/V (ethyl acetate)=6/1] detected that most of the raw material disappeared. Then, 1.30 mL of HOAc, 25 mL of isopropanol and 15 mL of ice water were sequentially added while the solution changed from turbid to clear, and stirred at room temperature for 0.5 hour. 40 mL of water was slowly dropwise added, and after completion of the dropwise addition, stirred at room temperature for 2 hours. A large number of white solid precipitated and was filtered. The filter cake was washed with a mixed solution of isopropyl alcohol/water=1:1 and dried under vacuum at 50° C. for 8 hours to obtain 4.05 g of methyl 2-chloro-6-(4-methoxyphenoxy) nicotinate as a solid, 91.84%.

Step 2: Preparation of methyl 2-ethyl-6-(4-methoxyphenoxy) nicotinate

A 100 ml dry three-necked flask was sequentially charged, under the protection of nitrogen, with methyl 2-chloro-6-(4-methoxyphenoxy) nicotinate (4.05 g, 13.79 mmol), 1,2-bis(diphenylphosphino)ethane nickel chloride (abbreviated as Ni(DPPE)Cl$_2$) (37 mg, 0.07 mmol) and 20 ml of dry tetrahydrofuran for dissolving them. 28 mL (28 mmol) of ethylmagnesium bromide (1 M, in tetrahydrofuran) was slowly dropwise added under stirring at room temperature in two portions at 0.5 hour intervals, and after completion of the dropwise addition, the mixture was stirred at room temperature for 0.5 hour. Thin layer chromatography [V (petroleum ether)/V (ethyl acetate)=7/1] detected that the reaction was basically completed. The reaction was quenched with 13 ml of 10% citric acid aqueous solution, and the reaction solution was partitioned between ethyl acetate and water, extracted with ethyl acetate (50 mL×2). The organic phases were combined, washed with saturated brine, dried over anhydrous sodium sulfate, and filtered. The filtrate was mixed with crude silica gel, and subjected to flash column chromatography on silica gel column, eluting with V (petroleum ether)/V (ethyl acetate)=30/1. The fraction was evaporated to dryness to obtain 3.05 g of methyl 2-ethyl-6-(4-methoxyphenoxy) nicotinate as a pale yellow oil, 77.15%.

Step 3: Preparation of methyl 2-(1-bromoethyl)-6-(4-methoxyphenoxy) nicotinate

A 100 mL eggplant flask was sequentially charged with methyl 2-ethyl-6-(4-methoxyphenoxy) nicotinate (3.05 g, 10.62 mmol), N-bromosuccinimide (2.08 g, 11.68 mmol), azobisisobutyronitrile (1.92 g, 11.68 mmol) and 15 ml of carbon tetrachloride for dissolving them. The mixture was refluxed for 2 hours under stirring. Thin layer chromatography [V (petroleum ether)/V (ethyl acetate)=7/1] detected that the reaction was completed, and the reaction solution was partitioned between dichloromethane and water, extracted with dichloromethane (50 mL×3). The organic phases were combined, washed with saturated brine, dried over anhydrous sodium sulfate, and filtered. The filtrate was mixed with crude silica gel, and subjected to flash column chromatography on silica gel column, eluting with V (petroleum ether)/V (ethyl acetate)=30/1. The fraction was evaporated to dryness to obtain methyl 2-(1-bromoethyl)-6-(4-methoxyphenoxy) nicotinate as a pale yellow oil, which was directly used in the next reaction.

Step 4: Preparation of methyl 2-(1-(N-(2-methoxy-2-oxoethyl)-4-toluenesulfonylamino)ethyl)-6-(4-methoxyphenoxy) nicotinate A 100 mL eggplant flask was sequentially charged with methyl 2-(1-bromoethyl)-6-(4-methoxyphenoxy) nicotinate (3.18 g, 8.69 mmol) prepared in step 3, p-toluenesulfonyl-glycine methyl ester (2.10 g, 8.69 mmol) and potassium carbonate (2.40 g, 17.38 mmol) and sodium iodide (131 mg, 0.87 mmol) and 20 ml of N,N-dimethylformamide for dissolving them. The mixture was stirred at 50° C. for 10 hours. Thin layer chromatography [V (petroleum ether)/V (ethyl acetate)=2/1] detected that the reaction was basically completed, and the reaction solution was partitioned between ethyl acetate and water, extracted with ethyl acetate (50 mL×3). The organic phases were combined, washed with saturated brine, dried over anhydrous sodium sulfate, and filtered. The filtrate was mixed with crude silica gel, and subjected to flash column chromatography on silica gel column, eluting with V (petroleum ether)/V (ethyl acetate)=4/1. The fraction was evaporated to dryness to obtain 2.06 g of methyl 2-(1-(N-(2-methoxy-2-oxoethyl)-4-toluenesulfonylamino)ethyl)-6-(4-methoxyphenoxy) nicotinate, 44.90%.

Step 5: Preparation of 5-hydroxy-2-(4-methoxyphenoxy)-8-methyl-1,7-naphthyridine-6-carboxylate A 50 mL single neck flask was charged with methyl 2-(1-(N-(2-methoxy-2-oxoethyl)-4-toluenesulfonylamino)ethyl)-6-(4-methoxyphen oxy) nicotinate (2.06 g, 3.90 mmol) and 10 mL of dimethyl sulfoxide for dissolving it. A solution of sodium methoxide in methanol (5 M, 1.6 ml, 8 mmol) was dropwise added and stirred for 0.5 hour. Thin layer chromatography [V (ethyl acetate)/V (dichloromethane)=1/20)] detected that the reaction was basically completed. The reaction solution was adjusted to pH 4 with dilute hydrochloric acid, and partitioned between dichloromethane and water, extracted with dichloromethane (50 mL×2). The organic phases were combined, washed with saturated brine, dried over anhydrous sodium sulfate, and filtered. The filtrate was mixed with crude silica gel, and subjected to flash column chromatography on silica gel column, eluting with V (dichloromethane)/V (ethyl acetate)=80/1. The fraction was evaporated to dryness to obtain 830 mg of 5-hydroxy-2-(4-methoxyphenoxy)-8-methyl-1,7-naphthyridine-6-formate as a white solid, 62.57%.

Step 6: Preparation of 2-(5-hydroxy-2-(4-methoxyphenoxy)-8-methyl-1,7-naphthyridine-6-formamido) acetic acid A 50 mL sealed reaction tube was sequentially charged with methyl 5-hydroxy-2-(4-methoxyphenoxy)-8-methyl-1,7-naphthyridine-6-carboxylate (270 mg, 0.80 mmol), glycine (180 mg, 2.40 mmol), a solution of sodium methoxide in methanol (5M, 0.5 ml, 2.5 mmol) and 6 mL of methanol. The mixture was stirred at 120° C. for 20 hours. LCMS detected that the reaction was basically completed. The reaction solution was adjusted with dilute hydrochloric acid to pH 4, the solution changed from yellow turbidity to clear and then back to yellow turbidity, and a solid precipitated and was filtered. The filter cake was washed with a large amount of water and a small amount of methanol and dried to obtain 78 mg of 2-(5-hydroxy-2-(4-methoxyphenoxy)-8-methyl-1,7-naphthyridine-6-formamido) acetic acid as a yellow solid, 25.65%.

1H NMR (400 MHz, DMSO-d6) δ 13.27 (s, 1H), 12.83 (s, 1H), 9.12 (t, J=6.2 Hz, 1H), 8.62 (d, J=9.0 Hz, 1H), 7.49 (d, J=9.0 Hz, 1H), 7.34-7.25 (m, 2H), 7.09-6.98 (m, 2H), 4.04 (d, J=6.2 Hz, 2H), 3.81 (s, 3H), 2.55 (s, 3H).

Example 10

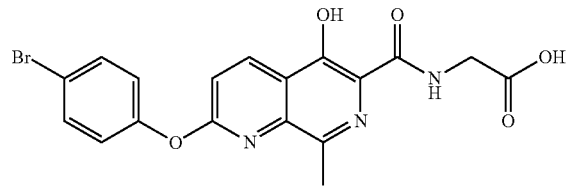 [SMILES: Cc1nc(C(=O)NCC(=O)O)c(O)c2ccc(Oc3ccc(Br)cc3)nc12]

Compound No. 10 (2-(2-(4-bromophenoxy)-5-hydroxy-8-methyl-1,7-naphthyridine-6-formamido) acetic acid Step 1: Preparation of methyl 6-(4-bromophenoxy)-2-chloronicotinate A 250 mL eggplant flask was sequentially charged with methyl 2,6-dichloronicotinate (8.24 g, 40 mmol), 4-bromophenol (6.92 g, 40 mmol), and 50 mL of N,N-dimethylformamide for dissolving them. Triethylamine (7.2 mL, 52 mmol) was added dropwise under stirring at room temperature, and after completion of the dropwise addition, triethylene diamine (672 mg, 6 mmol) was added. The mixture was stirred at room temperature for 4-5 hours and the solution changed from clear to turbid. Thin layer chromatography [V (petroleum ether)/V (ethyl acetate)=6/1] detected that most of the raw material disappeared. Then, 1.30 mL of HOAc, 25 mL of isopropanol and 15 mL of ice water were sequentially added while the solution changed from turbid to clear, and stirred at room temperature for 0.5 hour. 40 mL of water was slowly dropwise added, and after completion of the dropwise addition, stirred at room temperature for 2 hours. A large number of white solid precipitated and was filtered. The filter cake was washed with a mixed solution of isopropyl alcohol/water=1:1 and dried under vacuum at 50° C. for 8 hours to obtain 11.48 g of methyl 6-(4-bromophenoxy)-2-chloronicotinate as a solid, 83.92%.

Step 2: Preparation of methyl 6-(4-bromophenoxy)-2-ethylnicotinate

A 100 ml dry three-necked flask was sequentially charged, under the protection of nitrogen, with methyl 6-(4-bromophenoxy)-2-chloronicotinate (1.03 g, 3 mmol), 1,2-bis(diphenylphosphino)ethane nickel chloride (abbreviated as Ni(DPPE)$Cl_2$) (10 mg, 0.02 mmol) and 10 ml of dry tetrahydrofuran for dissolving them. 6 ml of ethylmagnesium bromide (1 M, in tetrahydrofuran) was slowly dropwise added under stirring at room temperature in two portions at 0.5 hour intervals, and after completion of the dropwise addition, the mixture was stirred at room temperature for 0.5 hour. Thin layer chromatography [V (petroleum ether)/V (ethyl acetate)=7/1] detected that the reaction was basically completed. The reaction was quenched with 13 ml of 10% citric acid aqueous solution, and the reaction solution was partitioned between ethyl acetate and water, extracted with ethyl acetate (50 mL×2). The organic phases were combined, washed with saturated brine, dried over anhydrous sodium sulfate, and filtered. The filtrate was mixed with crude silica gel, and subjected to flash column chromatography on silica gel column, eluting with V (petroleum ether)/V (ethyl acetate)=30/1. The fraction was evaporated to dryness to obtain 790 mg of methyl 6-(4-bromophenoxy)-2-ethylnicotinate as a pale yellow oil, 78.07%.

Step 3: Preparation of methyl 2-(1-bromoethyl)-6-(4-bromophenoxy) nicotinate

A 100 mL eggplant flask was sequentially charged with methyl 6-(4-bromophenoxy)-2-ethylnicotinate (790 mg, 2.35 mmol), N-bromosuccinimide (461 mg, 2.59 mmol), azobisisobutyronitrile (425 mg, 2.59 mmol) and 15 ml of carbon tetrachloride for dissolving them. The mixture was refluxed for 2 hours under stirring. Thin layer chromatography [V (petroleum ether)/V (ethyl acetate)=7/1] detected that the reaction was completed, and the reaction solution was partitioned between dichloromethane and water, extracted with dichloromethane (50 mL×3). The organic phases were combined, washed with saturated brine, dried over anhydrous sodium sulfate, and filtered. The filtrate was mixed with crude silica gel, and subjected to flash column chromatography on silica gel column, eluting with V (petroleum ether)/V (ethyl acetate)=30/1. The fraction was evaporated to dryness to obtain methyl 2-(1-bromoethyl)-6-(4-bromophenoxy) nicotinate as a pale yellow oil, which was directly used in the next reaction.

Step 4: Preparation of methyl 6-(4-bromophenoxy)-2-(1-(N-(2-methoxy-2-oxoethyl)-4-toluenesulfonylamino) ethyl) nicotinate A 100 mL eggplant flask was sequentially charged with methyl 2-(1-bromoethyl)-6-(4-bromophenoxy) nicotinate (890 mg, 2.14 mmol) prepared in step 3, p-toluenesulfonylglycine methyl ester (518 mg, 2.14 mmol) and potassium carbonate (591 mg, 4.28 mmol) and sodium iodide (32 mg, 0.21 mmol) and 15 ml of N,N-dimethylformamide for dissolving them. The mixture was stirred at 50° C. for 10 hours. Thin layer chromatography [V (petroleum ether)/V (ethyl acetate)=2/1] detected that the reaction was basically completed, and the reaction solution was partitioned between ethyl acetate and water, extracted with ethyl acetate (50 mL×3). The organic phases were combined, washed with saturated brine, dried over anhydrous sodium sulfate, and filtered. The filtrate was mixed with crude silica gel, and subjected to flash column chromatography on silica gel column, eluting with V (petroleum ether)/V (ethyl acetate) =4/1. The fraction was evaporated to dryness to obtain 420 mg of methyl 6-(4-bromophenoxy)-2-(1-(N-(2-methoxy-2-oxoethyl)-4-toluenesulfonylamino) ethyl) nicotinate as a pale yellow solid, 33.94%.

Step 5: Preparation of methyl 2-(4-bromophenoxy)-5-hydroxy-8-methyl-1,7-naphthyridine-6-carboxylate A 50 mL single neck flask was charged with methyl 6-(4-bromophenoxy)-2-(1-(N-(2-methoxy-2-oxoethyl)-4-methylbenzenesulfonamido)ethyl) nicotinate (1.14 g, 2 mmol) and 10 mL of dimethyl sulfoxide for dissolving it. A solution of sodium methoxide in methanol (5 M, 0.8 ml, 4 mmol) was dropwise added and stirred for 0.5 hour. Thin layer chromatography [V (ethyl acetate)/V (dichloromethane)=1/20)] detected that the reaction was basically completed. The reaction solution was adjusted to pH 4 with dilute hydrochloric acid, and partitioned between dichloromethane and water, extracted with dichloromethane (50 mL×2). The organic phases were combined, washed with saturated brine, dried over anhydrous sodium sulfate, and filtered. The filtrate was mixed with crude silica gel, and subjected to flash column chromatography on silica gel column, eluting with V (dichloromethane)/V (ethyl acetate)=80/1. The fraction was evaporated to dryness to obtain 540 mg of methyl 2-(4-bromophenoxy)-5-hydroxy-8-methyl-1,7-naphthyridine-6-carboxylate as a white solid, 70.26%.

Step 6: Preparation of 2-(2-(4-bromophenoxy)-5-hydroxy-8-methyl-1,7-naphthyridine-6-formamido) acetic acid A 50 mL sealed reaction tube was sequentially charged with methyl 2-(4-bromophenoxy)-5-hydroxy-8-methyl-1,7-naphthyridine-6-carboxylate (290 mg, 0.75 mmol), glycine (169 mg, 2.25 mmol), a solution of sodium methoxide in methanol (5M, 0.5 ml, 2.5 mmol) and 6 mL of methanol. The mixture was stirred at 120° C. for 20 hours. LCMS detected that the reaction was basically completed. The reaction solution was adjusted with dilute hydrochloric acid to pH 4, the solution changed from yellow turbidity to clear and then back to yellow turbidity, and a solid precipitated and was filtered. The filter cake was washed with a large amount of water and a small amount of methanol and dried to obtain 108 mg of 2-(2-(4-bromophenoxy)-5-hydroxy-8-methyl-1,7-naphthyridine-6-formamido) acetic acid as a yellow solid, 33.53%.

1H NMR (400 MHz, DMSO-d6) δ 13.28 (s, 1H), 12.83 (s, 1H), 9.13 (t, J=6.2 Hz, 1H), 8.65 (d, J=8.9 Hz, 1H), 7.74-7.65 (m, 2H), 7.56 (d, J=8.9 Hz, 1H), 7.42-7.33 (m, 2H), 4.05 (d, J=6.2 Hz, 2H), 2.54 (s, 3H).

Example 11

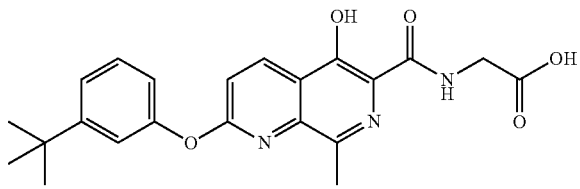 [SMILES: Cc1nc(C(=O)NCC(=O)O)c(O)c2ccc(Oc3cccc(C(C)(C)C)c3)nc12]

Compound No. 11 (2-(2-(3-(tert-butyl)phenoxy)-5-hydroxy-8-methyl-1,7-naphthyridine-6-formamido) acetic acid)

Step 1: Preparation of methyl 6-(3-(tert-butyl)phenoxy)-2-chloronicotinate

A 250 mL eggplant flask was sequentially charged with methyl 2,6-dichloronicotinate (3.09 g, 15 mmol), 3-(tert-butyl)phenol (2.25 g, 15 mmol), and 18 mL of N,N-dimethylformamide for dissolving them. Triethylamine (2.7 mL, 6.5 mmol) was added dropwise under stirring at room temperature, and after completion of the dropwise addition, triethylene diamine (252 mg, 0.75 mmol) was added. The mixture was stirred at room temperature for 4-5 hours and the solution changed from clear to turbid. Thin layer chromatography [V (petroleum ether)/V (ethyl acetate)=6/1] detected that most of the raw material disappeared. Then, 1.30 mL of HOAc, 25 mL of isopropanol and 15 mL of ice water were sequentially added while the solution changed from turbid to clear, and stirred at room temperature for 0.5 hour. 40 mL of water was slowly dropwise added, and after completion of the dropwise addition, stirred at room temperature for 2 hours. A large number of white solid precipitated and was filtered. The filter cake was washed with a mixed solution of isopropyl alcohol/water=1:1 and dried under vacuum at 50° C. for 8 hours to obtain 3.53 g of methyl 6-(3-(tert-butyl)phenoxy)-2-chloronicotinate as a solid, 73.77%.

Step 2: Preparation of methyl 6-(3-(tert-butyl)phenoxy)-2-ethylnicotinate

A 100 ml dry three-necked flask was sequentially charged, under the protection of nitrogen, with methyl 6-(3-(tert-butyl)phenoxy)-2-chloronicotinate (3.53 g, 11.04 mmol), 1,2-bis(diphenylphosphino)ethane nickel chloride (abbreviated as Ni(DPPE)Cl$_2$) (32 mg, 0.06 mmol) and 15 ml of dry tetrahydrofuran for dissolving them. 22 mL (22 mmol) of ethylmagnesium bromide (1 M, in tetrahydrofuran) was slowly dropwise added under stirring at room temperature in two portions at 0.5 hour intervals, and after completion of the dropwise addition, the mixture was stirred at room temperature for 0.5 hour. Thin layer chromatography [V (petroleum ether)/V (ethyl acetate)=7/1] detected that the reaction was basically completed. The reaction was quenched with 13 ml of 10% citric acid aqueous solution, and the reaction solution was partitioned between ethyl acetate and water, extracted with ethyl acetate (50 mL×2). The organic phases were combined, washed with saturated brine, dried over anhydrous sodium sulfate, and filtered. The filtrate was mixed with crude silica gel, and subjected to flash column chromatography on silica gel column, eluting with V (petroleum ether)/V (ethyl acetate)=30/1. The fraction was evaporated to dryness to obtain 3.09 g of methyl 6-(3-(tert-butyl) phenoxy)-2-ethylnicotinate as a pale yellow oil, 89.21%.

Step 3: Preparation of methyl 2-(1-bromoethyl)-6-(3-(tert-butyl)phenoxy) nicotinate A 100 mL eggplant flask was sequentially charged with methyl 6-(3-(tert-butyl)phenoxy)-2-ethylnicotinate (3.09 g, 9.86 mmol), N-bromosuccinimide (1.93 g, 10.85 mmol), azobisisobutyronitrile (1.78 g, 10.85 mmol) and 15 ml of carbon tetrachloride for dissolving them. The mixture was refluxed for 2 hours under stirring. Thin layer chromatography [V (petroleum ether)/V (ethyl acetate)=7/1] detected that the reaction was completed, and the reaction solution was partitioned between dichloromethane and water, extracted with dichloromethane (50 mL×3). The organic phases were combined, washed with saturated brine, dried over anhydrous sodium sulfate, and filtered. The filtrate was mixed with crude silica gel, and subjected to flash column chromatography on silica gel column, eluting with V (petroleum ether)/V (ethyl acetate)=30/1. The fraction was evaporated to dryness to obtain methyl 2-(l-bromoethyl)-6-(3-(tert-butyl)phenoxy) nicotinate as a pale yellow oil, which was directly used in the next reaction.

Step 4: Preparation of methyl 6-(3-(tert-butyl)phenoxy)-2-(1-(N-(2-methoxy-2-oxoethyl)-4-toluenesulfonylamino)ethyl) nicotinate A 100 mL eggplant flask was sequentially charged with methyl 2-(1-bromoethyl)-6-(3-(tert-butyl)phenoxy) nicotinate (3.42 g, 8.72 mmol) prepared in step 3, p-toluenesulfonylglycine methyl ester (2.11 g, 8.72 mmol) and potassium carbonate (2.41 g, 17.44 mmol) and sodium iodide (131 mg, 0.87 mmol) and 20 ml of N,N-dimethylformamide for dissolving them. The mixture was stirred at 50° C. for 10 hours. Thin layer chromatography [V (petroleum ether)/V (ethyl acetate)=2/1] detected that the reaction was basically completed, and the reaction solution was partitioned between ethyl acetate and water, extracted with ethyl acetate (50 mL×3). The organic phases were combined, washed with saturated brine, dried over anhydrous sodium sulfate, and filtered. The filtrate was mixed with crude silica gel, and subjected to flash column chromatography on silica gel column, eluting with V (petroleum ether)/V (ethyl acetate) =4/1. The fraction was evaporated to dryness to obtain 1.55 g of methyl 6-(3-(tert-butyl)phenoxy)-2-(1-(N-(2-methoxy-2-oxoethyl)-4-toluenesulfonylamino)ethyl) nicotinate as a pale yellow solid, 32.10%.

Step 5: Preparation of methyl 2-(3-(tert-butyl)phenoxy)-5-hydroxy-8-methyl-1,7-naphthyridine-6-carboxylate A 50 mL single neck flask was charged with methyl 6-(3-(tert-butyl) phenoxy)-2-(1-(N-(2-methoxy-2-oxoethyl)-4-toluenesulfonylamino)ethyl) nicotinate (1.55 g, 2.80 mmol) and 10 mL of dimethyl sulfoxide for dissolving it. A solution of sodium methoxide in methanol (5 M, 1.2 ml. 6 mmol) was dropwise added and stirred for 0.5 hour. Thin layer chromatography [V (ethyl acetate)/V (dichloromethane)=1/20)] detected that the reaction was basically completed. The reaction solution was adjusted to pH 4 with dilute hydrochloric acid, and partitioned between dichloromethane and water, extracted with dichloromethane (50 mL×2). The organic phases were combined, washed with saturated brine, dried over anhydrous sodium sulfate, and filtered. The filtrate was mixed with crude silica gel, and subjected to flash column chromatography on silica gel column, eluting with V (dichloromethane)/V (ethyl acetate)=80/1. The fraction was evaporated to dryness to obtain 630 mg of methyl 2-(3-(tert-butyl)phenoxy)-5-hydroxy-8-methyl-1,7-naphthyridine-6-carboxylate as a white solid, 61.63%.

Step 6: Preparation of 2-(2-(3-(tert-butyl)phenoxy)-5-hydroxy-8-methyl-1,7-naphthyridine-6-formamido) acetic acid A 50 mL sealed reaction tube was sequentially charged with methyl 2-(3-(tert-butyl)phenoxy)-5-hydroxy-8-methyl-1,7-naphthyridine-6-carboxylate (360 mg, 1 mmol), glycine (169 mg, 3 mmol), a solution of sodium methoxide in methanol (5 M, 0.6 ml, 3 mmol) and 6 mL of methanol. The mixture was stirred at 120° C. for 20 hours. LCMS detected that the reaction was basically completed. The reaction solution was adjusted with dilute hydrochloric acid to pH 4, the solution changed from yellow turbidity to clear and then back to yellow turbidity, and a solid precipitated and was filtered. The filter cake was washed with a large amount of water and a small amount of methanol and dried to obtain 108 mg of 2-(2-(3-(tert-butyl)phenoxy)-5-hydroxy-8-methyl-1,7-naphthyridine-6-formamido) acetic acid as a yellow solid, 26.85%.

1H NMR (400 MHz, DMSO-d6) δ 13.28 (s, 1H), 12.81 (s, 1H), 9.12 (t, J=6.2 Hz, 1H), 8.63 (d, J=9.0 Hz, 1H), 7.52 (d, J=9.0 Hz, 1H), 7.47-7.38 (m, 2H), 7.37-7.30 (m, 1H), 7.20-7.15 (m, 1H), 4.04 (d, J=6.2 Hz, 2H), 2.55 (s, 3H), 1.32 (s, 9H)

Example 12

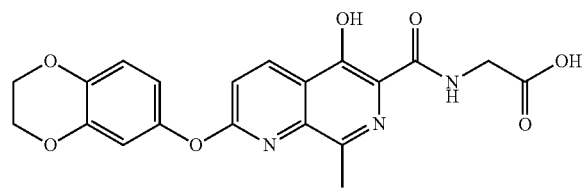 [SMILES: Cc1nc(C(=O)NCC(=O)O)c(O)c2ccc(Oc3ccc4c(c3)OCCO4)nc12]

Compound No. 12 (2-(2-((2,3-dihydrobenzo[b][1,4]dioxo-6-yl)oxy)-5-hydroxy-8-methyl-1,7-naphthyridine-6-formamido) acetic acid)

Step 1: Preparation of methyl 2-chloro-6-((2,3-dihydrobenzo[b][1,4]dioxo-6-yl)oxy) nicotinate A 250 mL eggplant flask was sequentially charged with methyl 2,6-dichloronicotinate (3.09 g, 15 mmol), 2,3-dihydrobenzo[b][1,4]dioxo-6-phenol (2.28 g, 15 mmol), and 18 mL of N,N-dimethylformamide for dissolving them. 2.7 mL (6.5 mmol) of triethylamine was added dropwise under stirring at room temperature, and after completion of the dropwise addition, 252 mg (0.75 mmol) of triethylene diamine was added. The mixture was stirred at room temperature for 4-5 hours and the solution changed from clear to turbid. Thin layer chromatography [V (petroleum ether)/V (ethyl acetate)=6/1] detected that most of the raw material disappeared. Then, 1.30 mL of HOAc, 25 mL of isopropanol and 15 mL of ice water were sequentially added while the solution changed from turbid to clear, and stirred at room temperature for 0.5 hour. 40 mL of water was slowly dropwise added, and after completion of the dropwise addition, stirred at room temperature for 2 hours. A large number of white solid precipitated and was filtered. The filter cake was washed with a mixed solution of isopropyl alcohol/water=1:1 and dried under vacuum at 50° C. for 8 hours to obtain 4.05 g of methyl 2-chloro-6-((2,3-dihydrobenzo[b][1,4]dioxo-6-yl) oxy) nicotinate as a solid, 84.11%.

Step 2: Preparation of methyl 6-((2,3-dihydrobenzo[b][1,4]dioxo-6-yl) oxy)-2-ethylnicotinate A 100 ml dry three-necked flask was sequentially charged, under the protection of nitrogen, with methyl 2-chloro-6-((2,3-dihydrobenzo[b][1,4]dioxo-6-yl)oxy) nicotinate (4.05 g, 12.62 mmol), 1,2-bis(diphenylphosphino)ethane nickel chloride (abbreviated as Ni(DPPE)Cl$_2$) (33 mg, 0.06 mmol) and 20 ml of dry tetrahydrofuran for dissolving them. 25 mL (25 mmol) of ethylmagnesium bromide (1 M, in tetrahydrofuran) was slowly dropwise added under stirring at room temperature in two portions at 0.5 hour intervals, and after completion of the dropwise addition, the mixture was stirred at room temperature for 0.5 hour. Thin layer chromatography [V (petroleum ether)/V (ethyl acetate)=7/1] detected that the reaction was basically completed. The reaction was quenched with 13 ml of 10% citric acid aqueous solution, and the reaction solution was partitioned between ethyl acetate and water, extracted with ethyl acetate (50 mL×2). The organic phases were combined, washed with saturated brine, dried over anhydrous sodium sulfate, and filtered. The filtrate was mixed with crude silica gel, and subjected to flash column chromatography on silica gel column, eluting with V (petroleum ether)/V (ethyl acetate)=30/1. The fraction was evaporated to dryness to obtain 2.65 g of methyl 6-((2,3-dihydrobenzo[b][1,4]dioxo-6-yl)oxy)-2-ethylnicotinate as a pale yellow oil, 66.68%.

Step 3: Preparation of methyl 2-(1-bromoethyl)-6-((2,3-dihydrobenzo[b][1, 4]dioxo-6-yl)oxy)nicotinate A 100 mL eggplant flask was sequentially charged with methyl 6-((2,3-dihydrobenzo[b][1,4]dioxo-6-yl) oxy)-2-ethylnicotinate (2.65 g, 8.41 mmol), N-bromosuccinimide (1.65 g, 9.25 mmol), azobisisobutyronitrile (1.52 g, 9.25 mmol) and 20 ml of carbon tetrachloride for dissolving them. The mixture was refluxed for 2 hours under stirring. Thin layer chromatography [V (petroleum ether)/V (ethyl acetate)=7/1] detected that the reaction was completed, and the reaction solution was partitioned between dichloromethane and water, extracted with dichloromethane (50 mL×3). The organic phases were combined, washed with saturated brine, dried over anhydrous sodium sulfate, and filtered. The filtrate was mixed with crude silica gel, and subjected to flash column chromatography on silica gel column, eluting with V (petroleum ether)/V (ethyl acetate)=30/1. The fraction was evaporated to dryness to obtain methyl 2-(1-bromoethyl)-6-((2,3-dihydrobenzo[b][1,4]dioxo-6-yl)oxy) nicotinate as a pale yellow oil, which was directly used in the next reaction.

Step 4: Preparation of methyl 6-((2,3-dihydrobenzo[b][1,4]dioxo-6-yl) oxy)-2-(1-(N-(2-methoxy-2-oxoethyl)-4-toluenesulfonylamino)ethyl) nicotinate A 100 mL eggplant flask was sequentially charged with methyl 2-(1-bromoethyl)-6-((2,3-dihydrobenzo[b][1,4]dioxo-6-yl)oxy) nicotinate (3.06 g, 7.77 mmol) prepared in step 3, p-toluenesulfonylglycine methyl ester (1.88 g, 7.77 mmol) and potassium carbonate (2.14 g, 15.54 mmol) and sodium iodide (117 mg, 0.78 mmol) and 20 ml of N,N-dimethylformamide for dissolving them. The mixture was stirred at 50° C. for 10 hours. Thin layer chromatography [V (petroleum ether)/V (ethyl acetate)=2/1] detected that the reaction was basically completed, and the reaction solution was partitioned between ethyl acetate and water, extracted with ethyl acetate (50 mL×3). The organic phases were combined, washed with saturated brine, dried over anhydrous sodium sulfate, and filtered. The filtrate was mixed with crude silica gel, and subjected to flash column chromatography on silica gel column, eluting with V (petroleum ether)/V (ethyl acetate)=4/1. The fraction was evaporated to dryness to obtain 916 mg of methyl 6-((2,3-dihydrobenzo[b][1,4]dioxo-6-yl)oxy)-2-(1-(N-(2-methoxy-2-oxoethyl)-4-toluenesulfonylamino) ethyl) nicotinate as a pale yellow solid, 21.21%

Step 5: Preparation of methyl 2-((2,3-dihydrobenzo[b][1,4]dioxo-6-yl) oxy)-5-hydroxy-8-methyl-1,7-naphthyridine-6-carboxylate A 50 mL single neck flask was charged with methyl 6-((2,3-dihydrobenzo [b][1,4]dioxo-6-yl)oxy)-2-(1-(N-(2-methoxy-2-oxoethyl)-4-methyl benzenesulfonamido)ethyl) nicotinate (916 mg, 1.65 mmol) and 8 mL of dimethyl sulfoxide for dissolving it. A solution of sodium methoxide in methanol (5 M, 0.7 ml, 3.5 mmol) was dropwise added and stirred for 0.5 hour. Thin layer chromatography [V (ethyl acetate)/V (dichloromethane)=1/20)] detected that the reaction was basically completed. The reaction solution was adjusted to pH 4 with dilute hydrochloric acid, and partitioned between dichloromethane and water, extracted with dichloromethane (50 mL×2). The organic phases were combined, washed with saturated brine, dried over anhydrous sodium sulfate, and filtered. The filtrate was mixed with crude silica gel, and subjected to flash column chromatography on silica gel column, eluting with V (dichloromethane)/V (ethyl acetate)=80/1. The fraction was evaporated to dryness to obtain 280 mg of methyl 2-((2,3-dihydrobenzo[b][1,4]dioxo-6-yl)oxy)-5-hydroxy-8-methyl-1,7-naphthyridine-6-carboxylate as a white solid, 46.18%.

Step 6: Preparation of 2-(2-((2,3-dihydrobenzo[b][1,4]dioxo-6-yl)oxy)-5-hydroxy-8-methyl-1,7-naphthyridine-6-formamido) acetic acid A 50 mL sealed reaction tube was sequentially charged with methyl 2-((2,3-dihydrobenzo[b][1,4]dioxo-6-yl)oxy)-5-hydroxy-8-methyl-1,7-naphthyridine-6-carboxylate (280 mg, 0.76 mmol), glycine (171 mg, 2.28 mmol), a solution of sodium methoxide in methanol (5 M, 0.5 ml, 2.50 mmol) and 6 mL of methanol. The mixture was stirred at 120° C. for 20 hours. LCMS detected that the reaction was basically completed. The reaction solution was adjusted with dilute hydrochloric acid to pH 4, the solution changed from yellow turbidity to clear and then back to yellow turbidity, and a solid precipitated and was filtered. The filter cake was washed with a large amount of water and a small amount of methanol and dried to obtain 130 mg of 2-(2-((2,3-dihydrobenzo[b][1,4]dioxo-6-yl)oxy)-5-hydroxy-8-methyl-1,7-naphthyridine-6-formamido) acetic acid as a yellow solid, 41.57%.

1H NMR (400 MHz, DMSO-d6) δ 13.32 (s, 1H), 9.08 (t, J=5.8 Hz, 1H), 8.62 (d, J=9.0 Hz, 1H), 7.45 (d, J=9.0 Hz, 1H), 7.00-6.90 (m, 2H), 6.83 (dd, J=8.8, 2.8 Hz, 1H), 4.29 (s, 4H), 3.99 (d, J=5.8 Hz, 2H), 2.60 (s, 3H).

Example 13

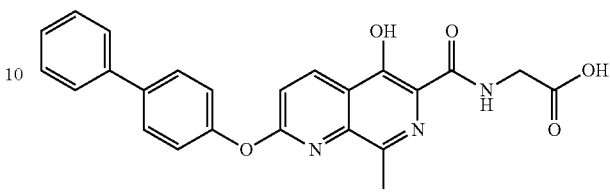

Compound No. 13 (2-(2-([1,1'-biphenyl]-4-oxo)-5-hydroxy-8-methyl-1,7-naphthyridine-6-formamido) acetic acid)

Step 1: Preparation of methyl 6-([1,1'-biphenyl]-4-oxo)-2-chloronicotinate

A 250 mL eggplant flask was sequentially charged with methyl 2,6-dichloronicotinate (4.12 g, 20 mmol), [1,1'-biphenyl]-4-phenol (3.40 g, 20 mmol), and 24 mL of N,N-dimethylformamide for dissolving them. Triethylamine (3.8 mL, 26 mmol) was added dropwise under stirring at room temperature, and after completion of the dropwise addition, triethylene diamine (336 mg, 3 mmol) was added. The mixture was stirred at room temperature for 4-5 hours and the solution changed from clear to turbid. Thin layer chromatography [V (petroleum ether)/V (ethyl acetate)=6/1] detected that most of the raw material disappeared. Then, 1.30 mL of HOAc, 25 mL of isopropanol and 15 mL of ice water were sequentially added while the solution changed from turbid to clear, and stirred at room temperature for 0.5 hour. 40 mL of water was slowly dropwise added, and after completion of the dropwise addition, stirred at room temperature for 2 hours. A large number of white solid precipitated and was filtered. The filter cake was washed with a mixed solution of isopropyl alcohol/water=1:1 and dried under vacuum at 50° C. for 8 hours to obtain 5.66 g of methyl 6-([1,1'-biphenyl]-4-oxo)-2-chloronicotinate as a solid, 83.24%.

Step 2: Preparation of methyl 6-[1,1'-biphenyl]-4-oxo)-2-ethylnicotinate

A 100 ml dry three-necked flask was sequentially charged, under the protection of nitrogen, with methyl 6-([1,1'-biphenyl]-4-oxo)-2-chloronicotinate (3.40 g, 10 mmol), 1,2-bis (diphenylphosphino)ethane nickel chloride (abbreviated as Ni(DPPE)Cl$_2$) (27 mg, 0.05 mmol) and 15 ml of dry tetrahydrofuran for dissolving them. 20 mL (20 mmol) of ethylmagnesium bromide (1 M, in tetrahydrofuran) was slowly dropwise added under stirring at room temperature in two portions at 0.5 hour intervals, and after completion of the dropwise addition, the mixture was stirred at room temperature for 0.5 hour. Thin layer chromatography [V (petroleum ether)/V (ethyl acetate)=7/1] detected that the reaction was basically completed. The reaction was quenched with 13 ml of 10% citric acid aqueous solution, and the reaction solution was partitioned between ethyl acetate and water, extracted with ethyl acetate (50 mL×2). The organic phases were combined, washed with saturated brine, dried over anhydrous sodium sulfate, and filtered. The filtrate was mixed with crude silica gel, and subjected to flash column chromatography on silica gel column, eluting with V (petroleum ether)/V (ethyl acetate)=30/1. The fraction was evaporated to dryness to obtain 2.78 g of methyl 6-[1,1'-biphenyl]-4-oxo)-2-ethylnicotinate as a pale yellow oil, 83.48%.

Step 3: Preparation of methyl 6-([1,1'-biphenyl]-4-oxo)-2-(1-bromoethyl) nicotinate A 100 mL eggplant flask was sequentially charged with methyl 6-[1,1'-biphenyl]-4-oxo)-2-ethylnicotinate (2.78 g, 8.34 mmol), N-bromosuccinimide (1.63 g, 9.17 mmol), azobisisobutyronitrile (1.50 g, 9.17 mmol) and 15 ml of carbon tetrachloride for dissolving them. The mixture was refluxed for 2 hours under stirring. Thin layer chromatography [V (petroleum ether)/V (ethyl acetate)=7/1] detected that the reaction was completed, and the reaction solution was partitioned between dichloromethane and water, extracted with dichloromethane (50 mL×3). The organic phases were combined, washed with saturated brine, dried over anhydrous sodium sulfate, and filtered. The filtrate was mixed with crude silica gel, and subjected to flash column chromatography on silica gel column, eluting with V (petroleum ether)/V (ethyl acetate)=30/1. The fraction was evaporated to dryness to obtain methyl 6-([1,1'-biphenyl]-4-oxo)-2-(1-bromoethyl) nicotinate as a pale yellow oil, which was directly used in the next reaction.

Step 4: Preparation of methyl 6-([1,1'-biphenyl]-4-oxo)-2-(1-(N-(2-methoxy-2-oxoethyl)-4-toluenesulfonylamino)ethyl) nicotinate A 100 mL eggplant flask was sequentially charged with methyl 6-([1,1'-biphenyl]-4-oxo)-2-(1-bromoethyl) nicotinate (3.14 g, 7.62 mmol) prepared in step 3, p-toluenesulfonylglycine methyl ester (1.85 g, 7.62 mmol) and potassium carbonate (2.10 g, 15.24 mmol) and sodium iodide (114 mg, 0.76 mmol) and 20 ml of N,N-dimethylformamide for dissolving them. The mixture was stirred at 50° C. for 10 hours. Thin layer chromatography [V (petroleum ether)/V (ethyl acetate)=2/1] detected that the reaction was basically completed, and the reaction solution was partitioned between ethyl acetate and water, extracted with ethyl acetate (50 mL×3). The organic phases were combined, washed with saturated brine, dried over anhydrous sodium sulfate, and filtered. The filtrate was mixed with crude silica gel, and subjected to flash column chromatography on silica gel column, eluting with V (petroleum ether)/V (ethyl acetate)=4/1. The fraction was evaporated to dryness to obtain 0.74 g of methyl 6-([1,1'-biphenyl]-4-oxo)-2-(1-(N-(2-methoxy-2-oxoethyl)-4-toluenesulfonylamino)ethyl) nicotinate as a pale yellow solid, 16.89%.

Step 5: Preparation of methyl 2-([1,1'-biphenyl]-4-oxo)-5-hydroxy-8-methyl-1,7-naphthyridine-6-carboxylate A 50 mL single neck flask was charged with methyl 6-([1,1'-biphenyl]-4-oxo)-2-(1-(N-(2-methoxy-2-oxoethyl)-4-toluenesulfonylamino) ethyl) nicotinate (740 mg, 1.29 mmol) and 5 mL of dimethyl sulfoxide for dissolving it. A solution of sodium methoxide in methanol (5 M, 0.5 ml, 2.5 mmol) was dropwise added and stirred for 0.5 hour. Thin layer chromatography [V (ethyl acetate)/V (dichloromethane)=1/20] detected that the reaction was basically completed. The reaction solution was adjusted to pH 4 with dilute hydrochloric acid, and partitioned between dichloromethane and water, extracted with dichloromethane (50 mL×2). The organic phases were combined, washed with saturated brine, dried over anhydrous sodium sulfate, and filtered. The filtrate was mixed with crude silica gel, and subjected to flash column chromatography on silica gel column, eluting with V (dichloromethane)/V (ethyl acetate)=80/1. The fraction was evaporated to dryness to 286 mg of methyl 2-([1,1'-biphenyl]-4-oxo)-5-hydroxy-8-methyl-1, 7-naphthyridine-6-carboxylate as a white solid, 57.57%.

Step 6: Preparation of 2-(2-([1,1'-biphenyl]-4-oxo)-5-hydroxy-8-methyl-1,7-naphthyridine-6-formamido) acetic acid A 50 mL sealed reaction tube was sequentially charged with methyl 2-([1,1'-biphenyl]-4-oxo)-5-hydroxy-8-methyl-1,7-naphthyridine-6-carboxylate (280 mg, 0.72 mmol), glycine (180 mg, 2.16 mmol), a solution of sodium methoxide in methanol (5M, 0.5 ml, 2.50 mmol) and 6 mL of methanol. The mixture was stirred at 120° C. for 20 hours. LCMS detected that the reaction was basically completed. The reaction solution was adjusted with dilute hydrochloric acid to pH 4, the solution changed from yellow turbidity to clear and then back to yellow turbidity, and a solid precipitated and was filtered. The filter cake was washed with a large amount of water and a small amount of methanol and dried to obtain 79 mg of 2-(2-([1,1'-biphenyl]-4-oxo)-5-hydroxy-8-methyl-1,7-naphthyridine-6-formamido) acetic acid, 25.39%.

1H NMR (400 MHz, DMSO-d6) δ 13.29 (s, 1H), 12.83 (s, 1H), 9.14 (t, J=6.2 Hz, 1H), 8.66 (d, J=9.0 Hz, 1H), 7.85-7.70 (m, 4H), 7.61-7.35 (m, 6H), 4.05 (d, J=6.2 Hz, 2H), 2.58 (s, 3H).

Example 14

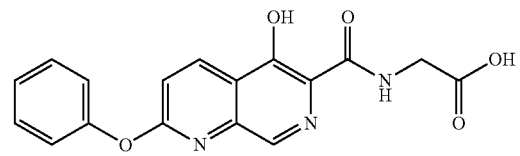 [SMILES: O=C(O)CNC(=O)c1ncc2nc(Oc3ccccc3)ccc2c1O]

Compound No. 6 (2-(5-hydroxy-2-phenoxy-1,7-naphthyridine-6-formamido) acetic acid)

Step 1: Preparation of methyl 2-chloro-6-phenoxypyridine-3-formate

A 250 mL eggplant flask was sequentially charged with 8.8 g (42.72 mmol) of methyl 2,6-dichloronicotinate, 4.02 g (42.72 mmol) of phenol, and 45 mL of N,N-dimethylformamide for dissolving them. 7.80 mL (55.54 mmol) of triethylamine was added dropwise under stirring at room temperature, and after completion of the dropwise addition, 720 mg (6.41 mmol) of triethylene diamine was added. The mixture was stirred at room temperature for 4-5 hours and the solution changed from clear to turbid. Thin layer chromatography [V (petroleum ether)/V (ethyl acetate)=6/1] detected that most of the raw material disappeared. Then, 1.30 mL (21.36 mmol) of HOAc, 25 mL of isopropanol and 15 mL of ice water were sequentially added while the solution changed from turbid to clear, and stirred at room temperature for 0.5 hour. 40 mL of water was slowly dropwise added, and after completion of the dropwise addition, stirred at room temperature for 2 hours. A large number of white solid precipitated and was filtered. The filter cake was washed with a mixed solution of isopropyl alcohol/water=1:1 and dried under vacuum at 50° C. for 8 hours to obtain 7.20 g of methyl 2-chloro-6-phenoxypyridine-3-formate.

Step 2: Preparation of methyl 2-methyl-6-phenoxypyridine-3-formate

A 100 ml dry three-necked flask was sequentially charged, under the protection of Argon (Ar), with 1.32 g (5 mmol) of methyl 2-chloro-6-phenoxypyridine-3-formate, 16 mg (0.03 mmol) of Ni(DPPE)Cl$_2$ and 5 ml of dry tetrahydrofuran for dissolving them. 11 mL (11 mmol) of ethylmagnesium bromide (1 M, in tetrahydrofuran) was slowly dropwise added under stirring at room temperature in two portions at 0.5 hour intervals, and after completion of the dropwise addition, the mixture was stirred at room temperature for 0.5 hour. Thin layer chromatography [V (petroleum ether)/V (ethyl acetate)=7/1] detected that the reaction was basically completed. The reaction was quenched with 13 ml of 10% citric acid aqueous solution, and the reaction solution was partitioned between ethyl acetate and water, extracted with ethyl acetate (50 mL×2). The organic phases were combined, washed with saturated brine, dried over anhydrous sodium sulfate, and filtered. The filtrate was mixed with crude silica gel, and subjected to flash column chromatography on silica gel column, eluting with V (petroleum ether)/V (ethyl acetate)=30/1. The fraction was evaporated to dryness to obtain 840 mg of methyl 2-methyl-6-phenoxypyridine-3-formate as a pale yellow oil.

Step 3: Preparation of methyl 2-(1-bromomethyl)-6-phenoxypyridine-3-formate

A 100 mL eggplant flask was sequentially charged with 659 mg (2.7 mmol) of methyl 2-methyl-6-phenoxypyridine-3-formate, 435 mg (4 mmol) of N-bromosuccinimide, 442 mg (19.83 mmol) of azobisisobutyronitrile and 20 ml of carbon tetrachloride for dissolving them. The mixture was refluxed for 2 hours under stirring. Thin layer chromatography [V (petroleum ether)/V (ethyl acetate)=7/1] detected that the reaction was completed, and the reaction solution was partitioned between dichloromethane and water, extracted with dichloromethane (50 mL×3). The organic phases were combined, washed with saturated brine, dried over anhydrous sodium sulfate, and filtered. The filtrate was mixed with crude silica gel, and subjected to flash column chromatography on silica gel column, eluting with V (petroleum ether)/V (ethyl acetate)=30/1. The fraction was evaporated to dryness to obtain 1.1 g of methyl 2-(1-bromomethyl)-6-phenoxypyridine-3-formate as a pale yellow oil, which was directly used in the next reaction.

Step 4: Preparation of methyl 2-(1-(N-(2-methoxy-2-oxoethyl)-4-toluenesulfonylamino) methyl)-6-phenoxypyridine-3-formate A 100 mL eggplant flask was sequentially charged with 1.1 g (3.4 mmol) of methyl 2-(1-bromomethyl)-6-phenoxypyridine-3-formate prepared in step 3, 575 mg (2.38 mmol) of p-toluenesulfonylglycine methyl ester and 700 mg of potassium carbonate and 51 mg (0.34 mmol) of sodium iodide and 6 ml of N, N-dimethylformamide for dissolving them. The mixture was stirred at 50° C. for 10 hours. Thin layer chromatography [V (petroleum ether)/V (ethyl acetate)=2/1] detected that the reaction was basically completed, and the reaction solution was partitioned between ethyl acetate and water, extracted with ethyl acetate (50 mL×3). The organic phases were combined, washed with saturated brine, dried over anhydrous sodium sulfate, and filtered. The filtrate was mixed with crude silica gel, and subjected to flash column chromatography on silica gel column, eluting with V (petroleum ether)/V (ethyl acetate)=4/1. The fraction was evaporated to dryness to obtain 700 mg of methyl 2-(1-(N-(2-methoxy-2-oxoethyl)-4-toluenesulfonylamino) methyl)-6-phenoxypyridine-3-formate as a pale yellow solid.

Step 5: Preparation of methyl 5-hydroxy-8-methyl-2-phenoxy-1,7-naphthyridine-6-formate A 50 mL single neck flask was charged with 483 mg (1.45 mmol) of methyl 2-(1-(N-(2-methoxy-2-oxoethyl)-4-methylbenzenesulfonylamino) methyl)-6-phenoxypyridine-3-formate and 5 mL of dimethyl sulfoxide for dissolving it. A solution of 0.32 ml of sodium methoxide in methanol (5M) was dropwise added and stirred for 0.5 hour. Thin layer chromatography [V (ethyl acetate)/V (dichloromethane)=1/20)] detected that the reaction was basically completed. The reaction solution was adjusted to pH 4 with dilute hydrochloric acid, and partitioned between dichloromethane and water, extracted with dichloromethane (50 mL×2). The organic phases were combined, washed with saturated brine, dried over anhydrous sodium sulfate, and filtered. The filtrate was mixed with crude silica gel, and subjected to flash column chromatography on silica gel column, eluting with V (dichloromethane)/V (ethyl acetate)=80/1. The fraction was evaporated to dryness to 340 mg of methyl 5-hydroxy-8-methyl-2-phenoxy-1,7-naphthyridine-6-formate as a white solid.

Step 6: Preparation of 2-(5-hydroxy-2-phenoxy-1,7-naphthyridine-6-formamido) acetic acid A 50 mL sealed reaction tube was sequentially charged with 100 mg (0.34 mmol) of methyl 5-hydroxy-2-phenoxy-1,7-naphthyridine-6-formate, 76 mg (0.02 mmol) of glycine, a solution of sodium methoxide in methanol (5 M, 0.13 ml) and 3 mL of methanol. The mixture was stirred at 120° C. for 20 hours. LCMS detected that the reaction was basically completed. The reaction solution was adjusted with dilute hydrochloric acid to pH 4, the solution changed from yellow turbidity to clear and then back to yellow turbidity, and a solid precipitated and was filtered. The filter cake was washed with a large amount of water and a small amount of methanol and dried to obtain 30 mg of 2-(5-hydroxy-2-phenoxy-1,7-naphthyridine-6-formamido) acetic acid as a white solid.

1H NMR (400 MHz, DMSO-d6) δ 13.62 (s, 1H), 12.82 (s, 1H), 9.39 (br s, 1H), 8.69 (d, J=8.9 Hz, 1H), 8.52 (s, 1H), 7.59 (d, J=9.0 Hz, 1H), 7.56-7.47 (m, 2H), 7.38-7.29 (m, 3H), 4.02 (d, J=6.1 Hz, 2H).

Biological Example 1: Promotion of Erythropoietin Expression In Vitro in Hepatoma Cells Hep3B by HIF-PHD2 Inhibitor Compounds The complete medium for culture of experimental hepatoma cells Hep3B (China Center for Type Culture Collection, CCTCC) was MEM (Cat# GNM 41500, GIBCO, provided by Hangzhou Genom Biopharmaceutical Technology Co., Ltd) supplemented with 10% serum FBS (Cat#10099-141, GIBCO) and 1% double-resistant P/S (Cat#GNM15140, provided by Hangzhou Genom Biopharmaceutical Technology Co., Ltd). Cells were cultured in a 37° C., 5% $CO_2$ incubator. Experimental reagents included dimethyl sulfoxide (for molecular biology, >=99.9%, Catalog# D8418) purchased from Sigma. The ELISA kit was purchased from Quantikine IVD ELISA, Human Erythropoietin (R&D, DEP00). The test control AKB-6548 was prepared by the inventors or obtained by commercial purchase. The test substance was stored at −20° C. in the dark.

The test substance and the positive control substance were fully dissolved in sterile water or dimethylsulfoxide under dark conditions and prepared into a stock solution at a concentration of $10^{-1}$ mol/L or $10^{-2}$ mol/L. Each of the stock solutions was stored at −20° C. MEM medium containing 0.5% FBS was used as a diluent to dilute the stock solution of the test substance, to prepare a diluted test substance at a concentration of 100 μmol/L and 10 μmol/L. To a 96-well culture plate was added 200 l/well (1.5 or $2.0\times10^4$ cells/well) of hepatoma cells Hep3B complete medium suspension and incubated overnight at 37° C. in a 5% $CO_2$ incubator. The solution in the 96-well culture plate was removed and the cells were washed once with the MEM medium containing 0.5% FBS. 200 μl/well of the test substance was added in the dark, at a dose of 100 μmol/L and 10 μmol/L, and each dose set 2 wells, a test well and a spare well. A cell control well was prepared by replacing the test solution with the diluent (without test substance and solvent). A solvent control well was prepared by replacing the test solution with the diluent containing the corresponding concentration of solvent (dimethylsulfoxide) (without test substance). They were cultured in a 5% $CO_2$ incubator at 37° C. for 24 hours. The supernatant was absorbed as a sample and cryopreserved at −20° C. for use. 100 μl/well of stop solution was added. OD value was detected by microplate reader A450 nm-A600 nm. The expression level of EPO (mIU/mL) promoted by the test substance was obtained according to the standard curve. The test results are shown in the following table:

| Compound No. | EPO level of the compounds of the invention/FG-4592 EPO level |
|---|---|
| 1 | 2.1 |
| 2 | 1.8 |
| 3 | 1.8 |
| 4 | 1.6 |
| 5 | 1.1 |
| 6 | 1.8 |
| 7 | 2.2 |
| 8 | 1.9 |
| 9 | 1.6 |
| 10 | 1.7 |
| 11 | 1 |
| 12 | 2 |
| 13 | 0.4 |

The biological activity test results show that compared to the positive control FG-4592, the compounds of the present invention have a more significant promotion effect on intracellular EPO expression, and most of the intracellular EPO levels reach more than 1.5 times of that of the positive control FG-4592.

Biological Example 2: Detection of Inhibitory Effect of the Compounds of the Invention on PHD2 ($IC_{50}$)

The interaction between hypoxia-inducible factor HIF-1α and VBC complex (von Hippel-Lindau protein-Elongin B-Elongin C, VBC) was detected by Fluorescence polarization (FP) method, to measure the enzyme inhibitory activity of the HIF Prolyl hydroxylases 2 (PHD2) inhibitor compounds.

To a NETN (20 mM Tris.HCl, 100 mM NaCl, 1 mM EDTA, 0.5% NP-40, 1 mM PMSF) buffer containing 200 μM ascorbic acid, 20 μM α-ketoglutaric acid, 100 μM $FeCl_2$ was added FAM-HIF (556-575) at a final concentration of 1 μM in the dark. Subsequently, the desired concentration of the test compound or the positive compound was added (the compound was replaced by the buffer in the negative control and the positive control). Finally, PHD2 was added at a final concentration of 0.5 μg/μl (PHD2 was replaced by the buffer in the negative control). They were mixed well and allowed to stand at room temperature for 30 minutes in the dark followed by 95° C. water bath for 1 minute, and then the reaction was terminated. After the temperature drops to room temperature, the sample was prepared well for use. EBC buffer (50 mM Tris.HCl, 120 mM NaCl, 0.5% NP-40) was added to the corresponding wells of a black 96-well test plate. A GST-VBC complex was added to the corresponding test wells at a final concentration of 300 nM (using the wells containing only EBC buffer as blank wells). Subsequently, the corresponding PHD2 prolyl hydroxylation reaction sample was added in the dark as a substrate with a final concentration of 100 nM. After mixing well, the lateral and longitudinal fluorescence intensity values were measured using a full-wavelength multifunctional microplate reader (TECAN infinite M1000) at an excitation wavelength of 407 nm and an emission wavelength of 518 nm.

The fluorescence polarization (mP) was calculated:

mP=1000×(lateral value−$G$ factor×longitudinal value)/(lateral value+$G$ factor×longitudinal value)

wherein, lateral value=lateral fluorescence intensity value of test well−lateral fluorescence intensity value of blank well, longitudinal value=longitudinal fluorescence intensity value of test well−longitudinal fluorescence intensity value of blank well, PHD2 inhibition rate (%) of the test compound was calculated according to the following formula:

Inhibition rate (%)=1−(mP test well−mP negative control well)/(mP positive control well−mP negative control well).

The $IC_{50}$ was calculated using the non-linear regression data analysis method of Graphpad Prism 4.0 software (Golden software, Golden, Colo., USA).

The experimental results show that the compounds of the present invention have HIF-prolyl hydroxylase inhibitory activity.

| Compound No. | $IC_{50}$ (μM) |
|---|---|
| 1 | 33 |
| 2 | 73 |

-continued

| Compound No. | IC$_{50}$ (μM) |
|---|---|
| 3 | 48 |
| 4 | 2.2 |
| 5 | 59 |
| 6 | 6.9 |
| 7 | 4 |
| 8 | 36 |
| 9 | 5.1 |
| 10 | 0.33 |
| 11 | 0.51 |
| 12 | 0.21 |
| 13 | 0.23 |
| 14 | 1.4 |

Biological Example 3: Effect of the Compounds of the Present Invention on Increasing Erythrocyte of Normal Mice 80 male Balb/c mice were divided into 11 groups, with 8 animals for each drug group, 10 animals for blank control group. Drug group: AKB-6548, 100 mg/kg, oral administration, once a day×3; FG-4592, 25 mg/kg, oral administration, once a day×3; EPO, 100 IU/kg, Day 1 and Day 3, subcutaneous injection, as positive control groups. Each of the compounds of the present invention was orally administrated at 25 mg/kg, once a day×3. Four hours after the last administration, orbital blood of all animals were collected and treated with EDTA-K2 anticoagulant, and reticulocytes (RETIC) were counted with a blood cell automated analyzer. The results show that the counts of the control compounds and the compounds of the present invention are higher than those of the normal animals (p<0.01), and the effects of partial compounds are higher effect than those of the small molecule positive control drug and EPO.

What is claimed is:

1. A compound having the following Formula (I) or a pharmaceutically acceptable salt thereof:

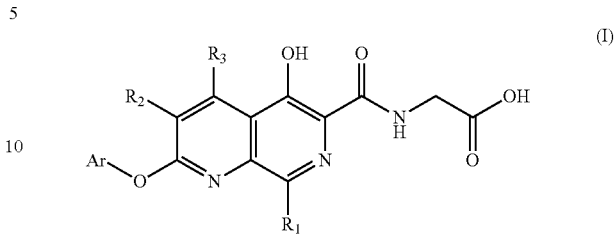

(I)

wherein,
R$_2$, R$_3$ are each independently hydrogen;
R$_1$ is hydrogen or C$_{1-3}$ alkyl;
Ar is an aromatic ring or an aromatic heterocyclic ring selected from the group consisting of a naphthalene ring, a pyridine ring, a thiophene ring, a furan ring and a substituted benzene ring;
wherein, the substituted benzene ring has the following structural formula:

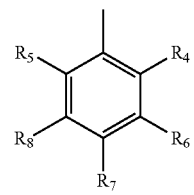

wherein R$_4$, R$_5$, R$_6$, R$_7$ and R$_8$ are independently selected from the group consisting of hydrogen, halogen, hydroxy, nitro, cyano and phenyl, C$_{1-7}$ alkyl, C$_{1-3}$ alkoxy, C$_{1-3}$ alkoxy optionally substituted by halogen, C$_{1-3}$ alkyl optionally substituted by halogen; or

| | | | Four hours after the last RETIC administration | | | |
|---|---|---|---|---|---|---|
| Mice No. # | Excipient control | AKB-6548-A (100 mg/kg) Oral, once a day × 3 | FG-4592-A (25 mg/kg) Oral, once a day × 3 | EPO (100 IU/kg) Subcutaneous injection, Day 1 and Day 3 | 14 (25 mg/kg) Oral, once a day × 3 | 12 (25 mg/kg) Oral, once a day × 3 | 1 (25 mg/kg) Oral, once a day × 3 |
| 1 | 3.2 | 4.2 | 4 | 4.3 | 4.4 | 4.3 | 4.1 |
| 2 | 2.6 | 5.3 | 3.4 | 5.1 | 4.9 | 5.6 | 4.1 |
| 3 | 3.3 | 5.3 | 3.6 | 5 | 5.8 | 5 | 4.9 |
| 4 | 3.3 | 6.1 | 3.8 | 5.9 | 6.1 | 5.4 | 4.4 |
| 5 | 4.1 | 4 | 3.8 | 2.5 | 6.6 | 5 | 5.2 |
| 6 | 1.5 | 4.2 | 4 | 2.2 | 5.8 | 6 | 4.8 |
| 7 | 2.3 | 4 | 3.5 | 2.6 | 6.5 | 5 | 5 |
| 8 | 1.4 | 4.9 | 4.4 | 2.2 | 5.7 | 5.6 | 5.3 |
| 9 | 2.4 | | | | | | |
| 10 | 1.8 | | | | | | |
| Average | 2.68 | 4.75 | 3.73 | 3.73 | 5.73 | 5.24 | 4.73 |
| SD | 0.89 | 0.77 | 0.24 | 1.51 | 0.75 | 0.52 | 0.47 |
| p1, in comparison with control | | 0.0001 | 0.0019 | 0.0633 | 0.0000 | 0.0000 | 0.0000 |
| p2, in comparison with AKB | | | 0.0069 | 0.1098 | 0.0228 | 0.1618 | 0.9388 |
| p3, in comparison with FG | | | | 0.8751 | 0.0000 | 0.0000 | 0.0005 |
| p4, in comparison with EPO | | | | | 0.0048 | 0.0181 | 0.0957 |

R<sub>6</sub> and R<sub>7</sub> form a ring, and form the following structural formula:

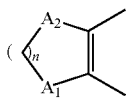

wherein, n is an integer of 1, 2, 3 or 4; $A_1$ and $A_2$ are each independently selected from the group consisting of oxygen, carbon and nitrogen atom.

2. The compound of claim 1 or a pharmaceutically acceptable salt thereof, wherein the pharmaceutically acceptable salt is a base addition salt.

3. The compound of claim 1 or a pharmaceutically acceptable salt thereof, wherein the compound has the following structural Formula (II):

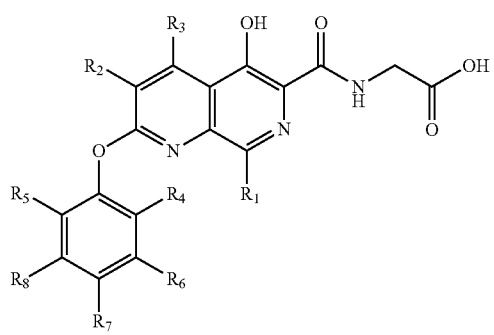

(II)

wherein $R_4$, $R_5$, $R_6$, $R_7$ and $R_8$ are independently selected from the group consisting of hydrogen, halogen, hydroxy, nitro, cyano and phenyl, $C_{1-7}$ alkyl, $C_{1-3}$ alkoxy, $C_{1-3}$ alkoxy optionally substituted by halogen, $C_{1-3}$ alkyl optionally substituted by halogen.

4. The compound of claim 1 or a pharmaceutically acceptable salt thereof, wherein the compound has the following Formula (III):

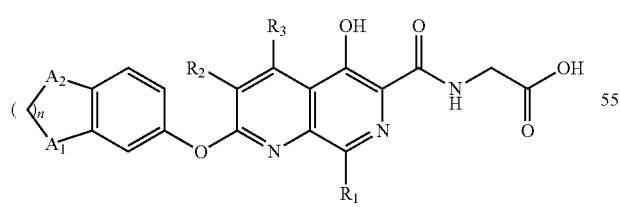

(III)

wherein, n is an integer of 1, 2, 3 or 4; $A_1$ and $A_2$ are each independently selected from the group consisting of oxygen, carbon and nitrogen atom.

5. The compound of claim 1 or a pharmaceutically acceptable salt thereof, wherein the compound is selected from the group consisting of:

| No. | Structure |
|---|---|
| 1 | 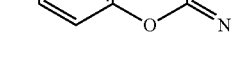 |
| 2 | 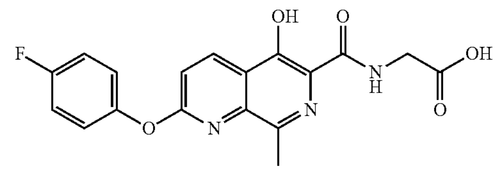 [SMILES: Cc1nc(C(=O)NCC(=O)O)c(O)c2ccc(Oc3ccc(F)cc3)nc12] |
| 3 | 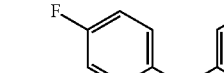 |
| 4 | 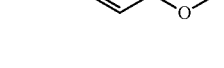 |
| 5 | 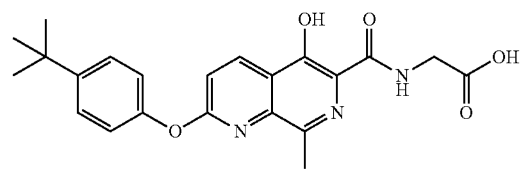 [SMILES: Cc1nc(C(=O)NCC(=O)O)c(O)c2ccc(Oc3ccc(C(C)(C)C)cc3)nc12] |
| 6 | 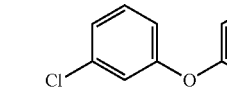 |
| 7 | 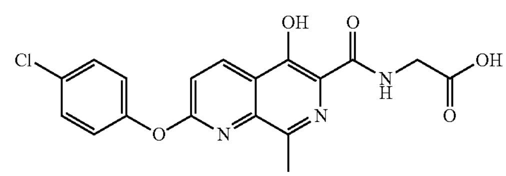 [SMILES: Cc1nc(C(=O)NCC(=O)O)c(O)c2ccc(Oc3ccc(Cl)cc3)nc12] |
| 8 | 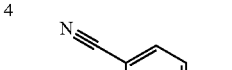 |
| 9 | 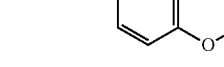 |

| No. | Structure |
|---|---|
| 10 | 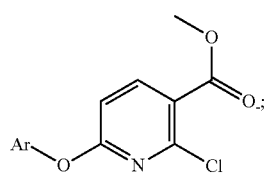 |
| 11 | (structure) |
| 12 | (structure) |
| 13 | (structure) |
| 14 | (structure) |

6. A method for preparing the compound of claim 1, comprising:

step 1: reacting methyl 2,6-dichloropyridine-3-formate with an aromatic phenol ArOH under basic conditions in the presence of a catalyst, to form an ether intermediate (IV)

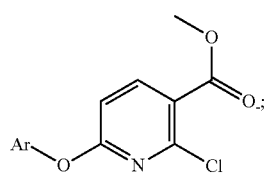

IV step 2: reacting the ether intermediate (IV) obtained in the step 1 and $R_1CH_2MgBr$ in the presence of a catalyst to perform the replacement of the chlorine atom by the alkyl, to form a methyl 2,6-disubstituted pyridine-3-formate intermediate (V)

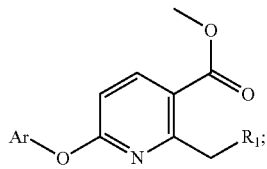

V step 3: brominating methyl or methylene group at the 2-position in the intermediate (V) obtained in the step 2 to obtain a brominated intermediate (VI);

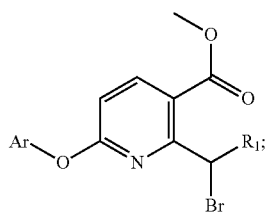

VI step 4: replacing the intermediate (VI) obtained in the step 3 with p-toluenesulfonylglycine methyl ester to obtain a p-toluenesulfonyl intermediate (VII)

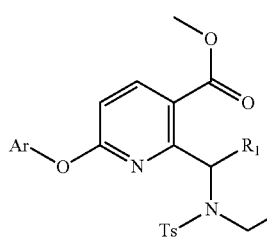

VII step 5: cyclizing the intermediate (VII) obtained in the step 4 under basic conditions to form a methyl 5-hydroxy-1,7-naphthyridine formate intermediate (VIII)

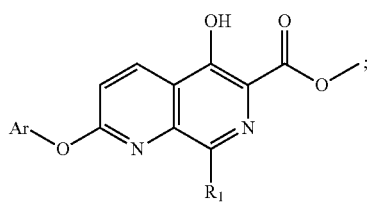

VIII step 6: reacting the intermediate (VIII) obtained in the step 5 with glycine to obtain a compound of Formula (I); wherein $R_1$, $R_2$, $R_3$ and Ar are as defined in claim 1.

7. The method of claim 6, wherein in the step 1, the basic condition comprises adding a base selected from the group consisting of triethylamine, diisopropylethylamine, the catalyst is selected from the group consisting of bicyclo[2.2.2]-1,4-diazacyclooctane and N, N-tetramethylethylenediamine; a preferred solvent is selected from the group consisting of N,N-dimethylformamide and N, N-dimethylacetamide;

in the step 2, the catalyst is 1,2-bis(diphenylphosphino)ethane nickel chloride; the step also comprises a reaction solvent selected from the group consisting of tetrahydrofuran and dioxane, the reaction temperature of the step is 0~50° C.;

in the step 3, the brominating reaction is carried out using a brominating reagent selected from the group consisting of N-bromosuccinimide, dibromohydantoin, cuprous bromide, and liquid bromine; the initiators for the bromination reaction is selected from the group consisting of azobisisobutyronitrile, benzoyl peroxide; the brominating reaction also comprises a solvent selected from the group consisting of carbon tetrachloride, dichloromethane and chloroform;

in the step 4, the base is selected from the group consisting of potassium carbonate, cesium carbonate, and sodium carbonate; the reaction solvent is selected from the group consisting of N, N-dimethylformamide, N-methylpyrrolidone, N, N-dimethylacetamide, and dimethylsulfoxide; the reaction temperature of the step is 20~80° C.;

in the step 5, the basic condition is formed by adding a base selected from the group consisting of sodium methoxide, sodium ethoxide, potassium tert-butoxide, and sodium tert-butoxide; the reaction solvent used in this step is selected from the group consisting of N, N-dimethylformamide, N-methylpyrrolidone, N, N-dimethylacetamide, dimethyl sulfoxide, methanol, ethanol, and tetrahydrofuran; the reaction temperature of the step is 0~40° C., the reaction time is 0.5~3 hours;

in the step 6, the basic condition is formed by adding a base selected from the group consisting of sodium methoxide, sodium ethoxide, potassium tert-butoxide, and sodium tert-butoxide; the reaction solvent used in this step is selected from the group consisting of methanol, ethanol, isopropanol, and n-butanol; the reaction temperature is 80~140° C.

8. A pharmaceutical composition, comprising a therapeutically effective amount of a compound of claim 1 or a pharmaceutically acceptable salt thereof, and a pharmaceutically acceptable carrier.

9. A method for inhibiting HIF prolyl hydroxylase, the method comprising administering the pharmaceutical composition of claim 8.

10. A method for promoting the generation of endogenous EPO, the method comprising administering the pharmaceutical composition of claim 8.

11. A method for stabilizing hypoxia-inducible factor α, the method comprising administering the pharmaceutical composition of claim 8.

12. A method for treating chronic disease-related anemia in a subject, the method comprising administering the pharmaceutical composition of claim 8.

13. The method of claim 12, wherein the chronic disease-related anemia is selected from the group consisting of rheumatoid arthritis, rheumatism and inflammatory bowel disease.

14. A method for increasing the production of inflammatory cytokines in a subject, the method comprising administering the pharmaceutical composition of claim 8.

15. The method of claim 14, wherein the inflammatory cytokines include tumor necrosis factor, interleukin and interferon.

16. A method for treating anemia in a subject that is resistant to the treatment of exogenous administration of erythropoietin, wherein the compound enhances the response of hematopoietic precursor cells to the erythropoietin, the method comprising administering the pharmaceutical composition of claim 8.

17. A method for increasing the production of a factor required for iron ingestion, iron transport and iron utilization in a subject, wherein the factor is selected from the group consisting of erythrocyte aminolevulinic acid synthase, transferrin, transferrin receptor and plasma ceruloplasmin, the method comprising administering the pharmaceutical composition of claim 8.

18. A method for inhibiting HIF prolyl hydroxylase in a subject, comprising administering to the subject a compound of claim 1 or a pharmaceutically acceptable salt thereof.

19. A method for promoting the generation of endogenous EPO in a subject, comprising administering to the subject a compound of claim 1 or a pharmaceutically acceptable salt thereof.

20. A method for stabilizing hypoxia-inducible factor α in a subject, comprising administering to the subject a compound of claim 1 or a pharmaceutically acceptable salt thereof.

21. A method for treating chronic disease-related anemia in a subject, comprising administering to the subject a compound of claim 1 or a pharmaceutically acceptable salt thereof.

22. The method of claim 21, wherein the chronic disease-related anemia is selected from the group consisting of rheumatoid arthritis, rheumatism and inflammatory bowel disease.

23. A method for increasing the production of inflammatory cytokines in a subject, comprising administering to the subject a compound of claim 1 or a pharmaceutically acceptable salt thereof.

24. The method of claim 23, wherein the inflammatory cytokines include tumor necrosis factor, interleukin and interferon.

25. A method for treating anemia in a subject that is resistant to the treatment of exogenous administration of erythropoietin, comprising administering to the subject a compound of claim 1 or a pharmaceutically acceptable salt thereof, wherein the compound enhances the response of hematopoietic precursor cells to the erythropoietin.

26. A method for increasing the production of a factor required for iron ingestion, iron transport and iron utilization in a subject, comprising administering to the subject a compound of claim 1 or a pharmaceutically acceptable salt thereof, wherein the factor is selected from the group consisting of erythrocyte aminolevulinic acid synthase, transferrin, transferrin receptor and plasma ceruloplasmin.

* * * * *